US012629337B2

(12) United States Patent
Fumic

(10) Patent No.: US 12,629,337 B2
(45) Date of Patent: May 19, 2026

(54) DAPTOMYCIN FORMULATION

(71) Applicant: Hikma Pharmaceuticals USA Inc., Berkeley Heights, NJ (US)

(72) Inventor: Barbara Fumic, Zagreb (HR)

(73) Assignee: Hikma Pharmaceuticals USA Inc., Berkeley Heights, NJ (US)

( * ) Notice: Subject to any disclaimer, the term of this patent is extended or adjusted under 35 U.S.C. 154(b) by 682 days.

(21) Appl. No.: 17/794,734

(22) PCT Filed: Feb. 26, 2021

(86) PCT No.: PCT/EP2021/054841

§ 371 (c)(1),
(2) Date: Jul. 22, 2022

(87) PCT Pub. No.: WO2021/170807

PCT Pub. Date: Sep. 2, 2021

(65) Prior Publication Data

US 2023/0068866 A1 Mar. 2, 2023

Related U.S. Application Data

(60) Provisional application No. 62/982,945, filed on Feb. 28, 2020.

(51) Int. Cl.
*A61K 38/12* (2006.01)
*A61K 9/19* (2006.01)
*A61K 47/18* (2017.01)

(52) U.S. Cl.
CPC ................ *A61K 9/19* (2013.01); *A61K 38/12* (2013.01); *A61K 47/183* (2013.01)

(58) Field of Classification Search
CPC ........... A61K 38/12; A61K 38/10; A61K 9/19
USPC ................................................ 514/21.6, 21.1
See application file for complete search history.

(56) References Cited

U.S. PATENT DOCUMENTS

| | | | | |
|---|---|---|---|---|
| 4,885,243 | A | 12/1989 | Huber et al. | |
| 8,835,382 | B2 | 9/2014 | O'Connor et al. | |
| 11,759,497 | B2 | 9/2023 | Bevetek Mocnik | |
| 12,053,502 | B2 * | 8/2024 | Mocnik .................. | A61K 38/12 |
| 2008/0286280 | A1 | 11/2008 | Kallmeyer et al. | |
| 2023/0068866 | A1 | 3/2023 | Fumic | |

FOREIGN PATENT DOCUMENTS

| | | | | |
|---|---|---|---|---|
| CN | 106943587 | A | 7/2017 | |
| IN | 2018/41024220 | * | 1/2020 | ............ A61K 38/12 |
| WO | 0197851 | A2 | 12/2001 | |
| WO | 2011062676 | A1 | 5/2011 | |
| WO | 2011063419 | A2 | 5/2011 | |
| WO | 2013103801 | A1 | 7/2013 | |
| WO | 2014041425 | A1 | 3/2014 | |
| WO | 2014045296 | A2 | 3/2014 | |
| WO | 2016098009 | A1 | 6/2016 | |
| WO | 2019043008 | A1 | 3/2019 | |

OTHER PUBLICATIONS

Goskonda, V. et al.; "Chemical Delivery Systems: Evaluation of Physicochemical Properties and Enzymatic Stability of Phenylephrone Derivatives"; Pharmaceutical Development and Technology, vol. 4, Issue No. 2; 1999; pp. 189-198; DOI: https://doi.org/10.1081/PDT-100101353.

Decision of Rejection received in CN 2018800556038 dated May 14, 2024.

Frankenfeld, C. et al.; "Daptomycin: a comparison of two intravenous formulations"; Drug Design, Development and Therapy, vol. 12; 2018; pp. 1953-1958.

International Search Report and Written Opinion for International Application PCT/EP2021/054841; International Filing Date: Feb. 26, 2021; Date of Mailing: Jun. 4, 2021; 9 pages.

Ajmera, A. et al.; "Stabilisation of proteins via mixtures of amino acids during spray drying"; International Journal of Pharmacuetics, vol. 403; 2014; pp. 98-107.

Anonymous; "Bulk Pharmaceutical Excipients—Certificate of Analysis"; Chapter 1080, DocId: 1_GUID-A25D8181-39A6-472F-8F3F-F1A823853321_3_en-US, available online at "https://online.uspnf.com/uspnf/document/1_GUID-A25D8181-39A6-472F-8F3F-F1A823853321_3_en-US"; 2021; 8 pages.

Huber, F. et al.; "The formation of daptomycin by supplying decanoic acid to *Streptomyces roseosporus* cultures producing the antibiotic complex A21978C"; Journal of Biotechnology, vol. 7; 1988; pp. 283-292.

International Search Report and Written Opinion; International Application No. PCT/EP2018/073141; International Filing Date Aug. 28, 2018; Date of Mailing Dec. 19, 2018; 14 pages.

Kirsch et al.; "Kinetics of the Aspartyl Transpeptidation of Daptomycin, a Novel Lipopeptide Antibiotic"; Pharmaceutical Research; 6(5); pp. 387-393; (1989).

Mattern, M. et al.; "Formulation of Proteins in Vacuum-Dried Glasses. II. Process and Storage Stability in Sugar-Free Amino Acid Systems"; Pharmaceutical Development and Technology, vol. 4, Issue No. 2; 1999; pp. 199-208.

Muangsiri et al., "The Kinetics of the Alkaline Degradation of Daptomycin"; Journal of Pharmaceutical Sciences; 90(8), pp. 1066-1075; (2001).

Muangsiri et al.; "Studies on the Reactions Between Daptomycin and Glyceraldehyde"; International Journal of Pharmaceutics; 289; pp. 133-150; (2005).

Tian, F. et al.; "Calorimetric investigation of protein/amino acid interactions in the solid state"; International Journal of Pharmaceutics, vol. 310; 2006; pp. 175-186.

(Continued)

*Primary Examiner* — Charanjit Aulakh

(74) *Attorney, Agent, or Firm* — Karen LeCuyer; DeWitt LLP

(57) ABSTRACT

The present disclosure relates to a solid formulation of daptomycin comprising at least one branched aliphatic amino acid. Solid daptomycin formulation of the present disclosure shows improved reconstituted time. The disclosure further relates to a method of preparation of the solid daptomycin formulation according to this disclosure.

27 Claims, No Drawings

(56) References Cited

OTHER PUBLICATIONS

Tian, F. et al.; "Spectroscopic evaluation of the stabilization of humanized monoclonal antibodies in amino acid formulations"; International Journal of Pharmaceutics, vol. 335; 2007; pp. 20-31.
Reifenberg P, Zimmer A. Branched-chain amino acids: physico-chemical properties, industrial synthesis and role in signaling, metabolism and energy production. Amino Acids. Aug. 28, 2024;56(1):51. doi: 10.1007/s00726-024-03417-2. PMID: 39198298; PMCID: PMC11358235.

* cited by examiner

DAPTOMYCIN FORMULATION

CROSS REFERENCE TO RELATED APPLICATIONS

This application is a National Stage application of PCT/EP2021/054841, filed Feb. 26, 2021, which claims priority to U.S. Provisional Application 62/982,945 filed Feb. 28, 2020, both of which are incorporated by reference in their entirety herein.

FIELD OF THE INVENTION

The present disclosure relates to a solid formulation of daptomycin comprising at least one branched aliphatic amino acid. Solid daptomycin formulation of the present disclosure shows improved reconstituted time. The disclosure further relates to a method of preparation of the solid daptomycin formulation according to this disclosure.

BACKGROUND OF THE INVENTION

Daptomycin is the first cyclic lipopeptide antibiotic approved by the U.S. Food and Drug Administration (FDA) in 2003 for the treatment of infections caused by Gram-positive pathogens, including methicillin- and vancomycin-resistant strains. Due to its unique mechanism of action, which is distinct from all other antimicrobial agents available in the market, daptomycin is able to overcome the mechanisms of resistance that many resistant strains have developed, and considering that rare incidences of clinical resistance to daptomycin are reported, the drug has become very important for current clinical practice.

Structure 1

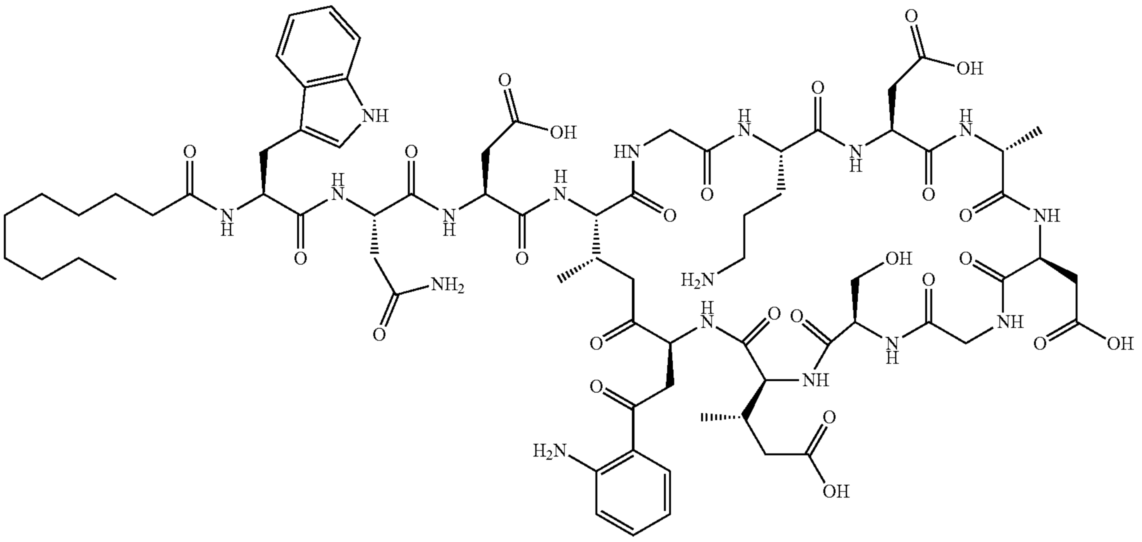

Molecular structure of daptomycin

Daptomycin is currently commercially available only in the form of lyophilized powder for intravenous infusion (Cubicin® and Cubicin RF®) which requires reconstitution and subsequent dilution prior to patient administration. Considering that reconstitution and dilution steps often take much of the time prior to administration to the patients, it is important that both steps are performed as quickly and as smoothly as possible.

According to available information of the present lyophilized daptomycin products on the market, reconstitution step often takes of about 30 minutes or even more for Cubicin® and about few minutes for Cubicin RF® (Frankenfeld et al, Drug Des Devel Ther, vol. 12, 2018, p 1953-1958).

The reconstitution time plays a critical role in injectable powders. Usually, the reconstitution time increases as the active compound amount increases, and thus, a short reconstitution time is an important goal in the development of high amount lyophilized active compound formulations. Short reconstitution time is preferable for both a member of medical institution and patients. If the reconstitution time is too long, it will increase the time needed for preparation and administration of a drug to a patient.

There still exists a need for lyophilized daptomycin compositions that exhibit improved reconstitution properties, such as a rapid reconstitution time in pharmaceutically acceptable solutions for reconstitution.

BRIEF DESCRIPTION OF THE INVENTION

The present disclosure relates to solid pharmaceutically acceptable formulations of daptomycin having improved reconstitution time, comprising at least one branched aliphatic amino acid or its pharmaceutically acceptable salts or derivatives thereof.

According to the present disclosure, it is found out that solid formulations of daptomycin comprising at least one excipient selected from branched aliphatic amino acids or their pharmaceutically acceptable salts or derivatives thereof have improved reconstitution properties. Specifically, solid pharmaceutically acceptable formulations of daptomycin according to the present disclosure have improved reconstitution time. Furthermore, In one aspect, solid pharmaceutically acceptable formulation of daptomycin may further have improved other properties, such as reduced foaming, reduced pH dependency for instance of reconstitution time. Further, In one aspect, improved reconstitution time of solid formulation of daptomycin according to the present disclosure does not significantly changes during storage.

According to this disclosure, branched aliphatic amino acids may include Leucine, Isoleucine and Valine.

In an aspect of the disclosure, stability of the solid daptomycin formulations comprising branched aliphatic amino acids as excipients for reducing reconstitution time may have comparable stability as the same solid daptomycin formulations not comprising any excipients for reducing reconstitution time.

DETAILED DESCRIPTION OF THE DISCLOSURE

The present disclosure relates to a solid pharmaceutically acceptable formulation of daptomycin having improved reconstitution time. The solid pharmaceutically acceptable formulation of daptomycin of the present disclosure comprises at least one excipient for reducing reconstitution time selected from branched aliphatic amino acids or their pharmaceutically acceptable salts or derivatives thereof.

The term "excipient for reconstitution" as used herein is to be understood to mean an excipient which reduce the time needed for reconstitution of the dried formulation. According to the present disclosure, excipient for reconstitution may reduce time for reconstitution to 150 seconds or less. According to the present disclosure, reduction of reconstitution time is achieved also when excipient for reconstitution is comprised in the formulation prior to drying in concentrations of 2.5% w/V or less. According to the present disclosure, terms "excipient for reconstitution and "excipient for reducing reconstitution time are used interchangeably. According to this disclosure, excipient for reconstitution include branched amino acid.

"Branched amino acids" as used herein, is to be understood to mean amino acids having an aliphatic side chain with a branch, i.e. where the central carbon atom is bound to three or more carbon atoms. In particular, branched amino acid is according to one aspect of the present disclosure selected from the group consisting of valine, leucin and isoleucine.

By terms "pharmaceutical formulation" or "pharmaceutically acceptable formulation" as used herein, is meant a composition that it is suitable for veterinary use as well as human pharmaceutical use, wherein such composition is generally safe, relatively non-toxic and does not cause unacceptable side effects, and contains pharmaceutically acceptable excipients, e.g. without limitation to solvents, carriers, antioxidants, surfactants, lipids, sugars, amino sugars, organic acids, complexing agents, preservatives, stabilizers, bulking agents, buffers, diluents, vehicles, solubilizers and binders. In an aspect, the formulation does not include an amino sugar excipient. In another aspect, the formulation does not include a surfactant, a sugar alcohol, an amino sugar, an organic solvent, a divalent cation, a cyclodextrin, or a combination thereof.

As used herein, the terms "pharmaceutical composition", "pharmaceutical formulation", "composition" and "formulation" are used interchangeably.

In one aspect, branched aliphatic amino acids include Valine, Isoleucine and Leucine, their pharmaceutically acceptable salts or derivatives thereof.

In one aspect, pharmaceutically acceptable salts of branched aliphatic amino acids may include hydrochloride salt, acetic salt, citric salt, phosphoric salt, succinic salt, tartaric salt and sulphuric salt thereof.

In one aspect, at least one branched aliphatic amino acid is selected from L-Valine, L-Leucine and L-Isoleucine, their pharmaceutically acceptable salts or derivatives thereof. In one aspect, at least one branched aliphatic amino acid is L-Isoleucine its pharmaceutically acceptable salts or derivatives thereof. In yet another aspect, at least one excipient is L-Valine, its pharmaceutically acceptable salts or derivatives thereof. In one aspect, at least one branched aliphatic amino acid is L-Leucine its pharmaceutically acceptable salts or derivatives thereof.

As used herein, "reconstitution time" is time measured from the point of adding reconstitution solution until entire cake of the solid daptomycin formulation is dissolved.

Unless otherwise stated, the term "adding reconstitution solution" means adding entire prescribed volume of the reconstitution solution.

Reconstitution time may be determined, for example, by adding 10 mL of Sterile Water for Injection, 0.9% Sodium chloride or Bacteriostatic Water for Injection to a unit dosage vial comprising the daptomycin pharmaceutical formulation. Immediately after adding the appropriate reconstitution solution (e.g., water, saline, etc.), a timer is started. The vial is rotated or swirled for a certain amount of time, as needed, to obtain a completely reconstituted solution. At that point, the timer is stopped and the reconstitution time is acknowledged.

Improved reconstitution time of the solid pharmaceutical formulation of daptomycin of the present disclosure may be presented as a percentage of reduction of the reconstitution time of the solid formulation of daptomycin comprising at least one branched aliphatic amino acid according to the present disclosure in relation to the reconstitution time of other solid daptomycin formulation.

As used herein, the terms "improved reconstitution time" and "reduced reconstitution time" are used interchangeably.

Other solid daptomycin formulation may be a referenced daptomycin product on the market or other generic daptomycin product on the market. Further, other solid daptomycin formulation which may be used for reconstitution time comparison purposes could be the same daptomycin formulation but not comprising excipient for reducing reconstitution time selected from branched aliphatic amino acids or their pharmaceutically acceptable salts or derivatives thereof.

Improved reconstitution time may also be interpreted as the time needed for reconstitution.

The reduced reconstitution time may be characterized by a reconstitution time not exceeding 300 seconds, or not exceeding 240 seconds, or not exceeding 180 seconds, or not exceeding 150 seconds, or not exceeding 120 seconds, or not exceeding 90 seconds, or not exceeding 80 seconds, or not exceeding 60 seconds or not exceeding 50 seconds.

In one aspect, the improved reconstitution time of solid daptomycin formulation do not exceed 150 seconds.

In one aspect, the improved reconstitution time of solid daptomycin formulation do not exceed 120 seconds.

In one aspect, the improved reconstitution time of solid daptomycin formulation is 90 seconds or less.

In one aspect, the improved reconstitution time of solid daptomycin formulation do not exceed one minute.

In one aspect, the improved reconstitution time for 500 mg of the solid pharmaceutical daptomycin formulation of the present disclosure in 10 mL of reconstitution solution at controlled room temperature is 120 seconds or less.

In one aspect, the improved reconstitution time for 500 mg of the solid pharmaceutical daptomycin formulation of the present disclosure in 10 mL of 0.9% sodium chloride at controlled room temperature is less than 120 seconds.

By term "controlled room temperature" used herein, is a controlled room temperature as set in USP <659>, i.e. from 20 to 25° C.

In one aspect, the improved reconstitution time for 500 mg of the solid pharmaceutically acceptable daptomycin formulation of the present disclosure in 10 mL of 0.9% sodium chloride at controlled room temperature is one minute or less.

In yet another aspect, reconstitution time for 500 mg of the solid pharmaceutically acceptable daptomycin formulation of the present disclosure in 10 mL of 0.9% sodium chloride at controlled room temperature can be 55 sec, 50 sec, 45 sec, 40 sec, 35 sec or 30 sec.

In one aspect, the improved reconstitution time for 500 mg of the solid pharmaceutically acceptable daptomycin formulation of the present disclosure in 10 mL of Water for injection at controlled room temperature is 120 seconds or less.

In one aspect, the improved reconstitution time for 500 mg of the solid pharmaceutically acceptable daptomycin formulation of the present disclosure in 10 mL of Water for injection at controlled room temperature is one minute or less.

In yet another aspect, reconstitution time for 500 mg of the solid pharmaceutically acceptable daptomycin formulation of the present disclosure in 10 mL of Water for injection at controlled room temperature can be 55 sec, 50 sec, 45 sec, 40 sec, 35 sec or 30 sec.

In another aspect, reconstitution time for 350 mg of the solid pharmaceutically acceptable daptomycin formulation in 7 mL of 0.9% sodium chloride at controlled room temperature is less than 50 seconds. In yet another aspect of the disclosure, reconstitution time for 350 mg of the solid pharmaceutically acceptable daptomycin composition in 7 mL of 0.9% sodium chloride at controlled room temperature can be 55 sec, 50 sec, 45 sec, 40 sec, 35 sec or 30 sec.

In yet another aspect, reconstitution time for 350 mg of the solid pharmaceutically acceptable daptomycin composition in 7 mL of Water for injection at controlled room temperature can be 55 sec, 50 sec, 45 sec, 40 sec, 35 sec or 30 sec.

In another aspect, reconstitution time for 3500 mg of the solid pharmaceutically acceptable daptomycin formulation in 70 mL of Water for injection at controlled room temperature is 120 seconds or less. In yet another aspect, reconstitution time for 3500 mg of the solid pharmaceutically acceptable daptomycin composition in 70 mL of Water for injection at controlled room temperature can be 90 seconds or less.

In various embodiments, the solid pharmaceutically acceptable formulation of the present disclosure is characterized by a reconstitution time that does not exceed 50 seconds. In some embodiments, the maximum reconstitution time of the solid pharmaceutically acceptable formulations of daptomycin of the present disclosure does not exceed 45 seconds.

In some embodiments, the maximum reconstitution time of the solid pharmaceutically acceptable formulations of daptomycin of the present disclosure does not exceed 40 seconds. In further embodiments, the maximum reconstitution time of the solid pharmaceutically acceptable formulations of daptomycin of the present disclosure does not exceed 35 seconds.

In one aspect, reconstitution time for 500 mg of daptomycin in the solid pharmaceutical formulation according to the present disclosure comprising L-Valine or L-Isoleucine in 10 mL of Water for injection at controlled room temperature is 120 seconds or less.

In one aspect, reconstitution time for 500 mg of daptomycin in the solid pharmaceutical formulation according to the present disclosure comprising L-Valine or L-Isoleucine in 10 mL of 0.9% sodium chloride at controlled room temperature is 120 seconds or less.

In one aspect, solid formulation of daptomycin including branched aliphatic amino acids may have from 96% to 60% reduced reconstitution time compared to the reconstitution time of Cubicin RLD.

According to this disclosure, by term "Cubicin RLD" is meant the solid daptomycin formulation on the market which is stored on refrigerated conditions and having as an inactive ingredient only sodium hydroxide for pH adjustment.

In one aspect, solid formulation of daptomycin including branched aliphatic amino acids may have from 96% to 60% reduced reconstitution time compared to the reconstitution time of the solid daptomycin formulation which is stored on refrigerated conditions and is having as an inactive ingredient only sodium hydroxide for pH adjustment.

In one aspect, solid formulation of daptomycin including branched aliphatic amino acids may have from 96% to 80% reduced reconstitution time compared to the reconstitution time of the solid daptomycin formulation which is stored on refrigerated conditions and is having as an inactive ingredient only sodium hydroxide for pH adjustment.

In one aspect, solid formulation of daptomycin including branched aliphatic amino acids may have from 96% to 60% reduced reconstitution time compared to the reconstitution time of the solid daptomycin formulation which does not contain excipients for reconstitution time.

In one aspect, solid formulation of daptomycin including branched aliphatic amino acids may have from 96% to 60% reduced reconstitution time compared to the reconstitution time of the solid daptomycin formulation which does not contain branched aliphatic amino acids.

In one aspect, solid formulation of daptomycin including branched aliphatic amino acids may have from 96% to 80% reduced reconstitution time compared to the reconstitution time of Cubicin RLD.

In one aspect, solid formulation of daptomycin including branched aliphatic amino acids may have from 96% to 82% reduced reconstitution time compared to the reconstitution time of Cubicin RLD.

In one aspect, solid formulation of daptomycin including branched aliphatic amino acids may have 10% or more reduced reconstitution time compared to the reconstitution time of the same solid formulation of daptomycin not comprising branched aliphatic amino acids.

In one aspect, solid formulation of daptomycin including branched aliphatic amino acids may have 25% or more reduced reconstitution time compared to the reconstitution time of the same solid formulation of daptomycin not comprising branched aliphatic amino acids.

In one aspect, solid formulation of daptomycin comprising branched aliphatic amino acids have 50% or more reduced reconstitution time compared to the reconstitution time of the same solid formulation of daptomycin not comprising branched aliphatic amino acids.

In one aspect, solid formulation of daptomycin comprising branched aliphatic amino acids have 70% or more reduced reconstitution time compared to the reconstitution time of the same solid formulation of daptomycin not comprising branched aliphatic amino acids.

In one aspect, solid formulation of daptomycin comprising L-Isoleucine may have 25% or more reduced reconstitution time compared to the reconstitution time of same solid formulation of daptomycin formulation not comprising L-Isoleucine.

In one aspect, solid formulation of daptomycin comprising L-Isoleucine may have 35% or more reduced reconstitution time compared to the reconstitution time of the same solid formulation of daptomycin formulation not comprising L-Isoleucine.

In one aspect, solid formulation of daptomycin comprising L-Isoleucine may have 50% or more reduced reconstitution time compared to the reconstitution time of the same solid formulation of daptomycin formulation not comprising L-Isoleucine.

In one aspect, solid formulation of daptomycin comprising L-Isoleucine may have 70% or more reduced reconstitution time compared to the reconstitution time of the same solid formulation of daptomycin formulation not comprising L-Isoleucine.

In one aspect, solid formulation of daptomycin comprising L-Valine may have 25% or more reduced reconstitution time compared to the reconstitution time of the same solid formulation of daptomycin formulation not comprising L-Valine.

In one aspect, solid formulation of daptomycin comprising L-Valine may have 50% or more reduced reconstitution time compared to the reconstitution time of the same solid formulation of daptomycin formulation not comprising L-Valine.

In one aspect, solid formulation of daptomycin comprising L-Valine may have 70% or more reduced reconstitution time compared to the reconstitution time of the same solid formulation of daptomycin formulation not comprising L-Valine.

In one aspect, solid formulation of daptomycin comprising L-Leucine may have 25% or more reduced reconstitution time compared to the reconstitution time of the same solid formulation of daptomycin formulation not comprising L-Leucine.

In one aspect, solid formulation of daptomycin comprising L-Leucine may have 35% or more reduced reconstitution time compared to the reconstitution time of the same solid formulation of daptomycin formulation not comprising L-Leucine.

In one aspect, solid formulation of daptomycin comprising L-Leucine may have 50% or more reduced reconstitution time compared to the reconstitution time of the same solid formulation of daptomycin formulation not comprising L-Leucine.

In one aspect, solid formulation of daptomycin comprising L-Leucine may have 70% or more reduced reconstitution time compared to the reconstitution time of the same solid formulation of daptomycin formulation not comprising L-Leucine.

According to the present disclosure, solid daptomycin formulation prior to drying contains low amount of excipient for reducing reconstitution time. By the term "low amount" of excipient for reducing reconstitution time according to the present disclosure is meant a concentration of the excipient for reconstitution time contained in the daptomycin formulation before drying which is 2.5% w/V or less. Low concentration of reconstituting excipient can be useful for various reasons as to influence on osmolality, providing a finished product with less concentration of excipients in total. The latter might be relevant for patient safety for patients in need of administering daptomycin. Furthermore, low concentration of the excipient useful in reducing reconstitution time according to the present disclosure may be useful when selecting reconstitution solution, e.g. in respect of the increased variety of optional type of reconstitution solution and/or in the amount of reconstitution solution needed.

Furthermore, branched aliphatic amino acids used in the present disclosure as excipients for reducing reconstitution time might be safer for use in wider population of patients than excipients used for reducing of reconstitution of time in other daptomycin formulations on the market.

In one aspect, the daptomycin formulation before drying comprises 2.5% w/V or less of the excipient for reducing reconstitution time. In one aspect, daptomycin formulation before draying comprises 2.4% w/V or less of the excipient for improving reconstitution time. In one aspect, the daptomycin formulation comprises 2.4% w/V, 2.3% w/V, 2% w/V, 1.8% w/V, 1.6% w/V, 1.5% w/V, 1.3% w/V, 1.2% w/V, 1.1% w/V, 1% w/V, 0.9% w/V, 0.8% w/V, 0.7% w/V, 0.6% w/V, 0.5% w/V, 0.4% w/V, 0.3% w/V, 0.2% w/V or 0.1% w/V of the excipient for improving reconstitution time before drying.

In one aspect, the daptomycin formulation before drying may comprise 1.5% w/V or less of the excipient for reducing reconstitution time. In one aspect, the daptomycin formulation before drying comprises 1% w/V or less of the excipient for reducing reconstitution time. In one aspect, the daptomycin formulation before drying may comprise 0.9% w/V, 0.8% w/V, 0.7% w/V, 0.6% w/V, 0.5% w/V, 0.4% w/V, 0.3% w/V, 0.2% w/V, 0.1% w/V or less of the excipient for reducing reconstitution time.

In one aspect the daptomycin formulation comprises 1% w/V or less of L-Isoleucine before drying. In one aspect the daptomycin formulation comprises 0.8% w/V or less of L-Isoleucine before drying. In one aspect the daptomycin formulation before drying comprises 10% w/V of daptomycin and 0.8% w/V of L-Isoleucine.

In one aspect the daptomycin formulation comprises 2.2% w/V or less of L-Valine before drying. In one aspect the daptomycin formulation comprises 0.7% w/V or less of L-Valine before drying. In one aspect the daptomycin formulation before drying comprises 10% w/V of daptomycin and 2.2% w/V of L-Valine.

In one aspect, the daptomycin formulation before drying comprises 10% w/V of daptomycin and 0.8% w/V of L-Isoleucine and has reconstitution time after drying of 120 seconds or less.

In one aspect, daptomycin formulation comprises 100 mg/ml to 400 mg/ml of daptomycin before drying.

As used herein, the term "% w/V" is defined as weight per volume percentage concentration of solution, i.e. as grams of solute per 100 mL of solution (g/100 mL).

In one aspect, at least one branched aliphatic amino acid is comprised in solid formulation of daptomycin in molar ratio to daptomycin from 0.5:1 to 5:1.

In one aspect, at least one branched aliphatic amino acid is comprised in solid formulation of daptomycin in molar ratio to daptomycin of 0.5:1, 1:1, 1.5:1, 2:1, 2.5:1, 3:1, 3.5:1, 4:1, 4.5:1, 5:1.

In one aspect, at least one excipient for reconstitution is comprised in solid formulation of daptomycin in molar ratio to daptomycin from 1:1 to 3:1.

In one aspect, L-Isoleucine is comprised in solid formulation of daptomycin in molar ratio to daptomycin from 1:1 to 3:1.

In one aspect, L-Isoleucine is comprised in solid formulation of daptomycin in molar ratio to daptomycin of 1:1, 1:2 or 3:1.

In one aspect, L-Isoleucine is comprised in solid formulation of daptomycin in molar ratio to daptomycin of 1:1.

In one aspect, L-Valine is comprised in solid formulation of daptomycin in molar ratio to daptomycin from 1:1 to 3:1.

In one aspect, L-Valine is comprised in solid formulation of daptomycin in molar ratio to daptomycin of 1:1, 1:2 or 3:1.

In one aspect, the daptomycin formulation before drying comprises 1% w/V or less of L-Isoleucine and the molar ratio of L-Isoleucine to daptomycin is 1:1.

In one aspect, the daptomycin formulation before drying comprises 1% w/V or less of L-Valine and the molar ratio of L-Valine to daptomycin is 1:1.

In one aspect, the daptomycin formulation before drying comprises 1% w/V or less of L-Valine and the molar ratio of L-Leucine to daptomycin is 1:1.

In one aspect, solid formulation of daptomycin comprises L-Isoleucine, wherein molar ratio of daptomycin to said excipient. i.e. Dapt:Ile, is 1:0.5 and wherein reconstitution time for 500 mg of solid daptomycin formulation in 10 mL of 0.9% sodium chloride injection at controlled room temperature (i.e. 20-25 degrees Celsius) is 90 seconds or less.

In one aspect, solid formulation of daptomycin comprises L-Isoleucine, wherein molar ratio of daptomycin to said excipient is Dapt:Ile 1:1 and wherein reconstitution time for 500 mg of solid daptomycin formulation in 10 mL of 0.9% sodium chloride injection at controlled room temperature (i.e. 20-25 degrees Celsius) is 120 seconds or less.

In one aspect, solid formulation of daptomycin comprises Isoleucine, wherein molar ratio of daptomycin to said excipient is Dapt:Ile 1:3 and wherein reconstitution time for 500 mg of solid daptomycin formulation in 10 mL of 0.9% sodium chloride at controlled room temperature (i.e. 20-25 degrees Celsius) is 150 seconds or less.

The solid composition of the present disclosure can be obtained by known processes of drying in the art, such as lyophilization, spray drying or bed drying of the liquid formulation of daptomycin in accordance with the present disclosure.

In one aspect, solid formulation of the present disclosure is obtained by lyophilization.

The terms "lyophilization," "lyophilized," and "freeze-dried" refer to a process by which the material to be dried is first frozen and then the ice or frozen solvent is removed by sublimation in a vacuum environment. Various excipients, including excipients for improvement of reconstitution time or excipients for stabilization of the formulation, may be included in pre-lyophilized formulations.

In one aspect, the reconstitution time of solid formulation of daptomycin comprising branched aliphatic amino acids is not substantially affected by the change of pH in predetermined pH ratio. According to the present disclosure, a term "predetermined pH ratio" means pH ratio of the daptomycin formulation prior to drying. In one aspect, the predetermined pH ration may be from 4.5 to 9. In other aspect, a predetermined pH ratio may be from 4.5 to 7. Yet, in other aspect, a predetermined pH ratio may be from 5.0 to 6.5.

In one aspect, targeted pH of aqueous formulations according to the present disclosure before drying is from 4.5 to 9.

In one aspect, targeted pH of aqueous formulations according to the present disclosure before drying is from 4.5 to 7.0.

In one aspect, the daptomycin formulation before drying comprises 2.4% w/V or less of at least one branched aliphatic amino acid and targeted pH of aqueous formulations according to the present disclosure before drying is from 4.5 to 7.0.

In one aspect, the daptomycin formulation before drying comprises 2.4% w/V or less of at least one branched aliphatic amino acid and targeted pH of aqueous formulations according to the present disclosure before drying is from 4.5 to 7.0 and where solid formulation of daptomycin has improved reconstitution time presented as for 60% to 96% reduced reconstitution time compared to the reconstitution time of Cubicin RLD.

In one aspect, the daptomycin formulation before drying comprises 2.4% w/V or less of at least one branched aliphatic amino acid and targeted pH of aqueous formulations according to the present disclosure before drying is from 4.5 to 7.0 and where solid formulation of daptomycin has improved reconstitution time presented as for 80% to 96% reduced reconstitution time compared to the reconstitution time of Cubicin RLD.

In one aspect, the daptomycin formulation before drying comprises 1% w/V or less of at least one branched aliphatic amino acid and targeted pH of aqueous formulations according to the present disclosure before drying is from 4.5 to 7.0.

In one aspect, the daptomycin formulation before drying comprises 2.4% w/V or less of L-Isoleucine and targeted pH of aqueous formulations according to the present disclosure before drying is from 4.5 to 7.0.

In one aspect, the daptomycin formulation before drying comprises 2.4% w/V or less of L-Isoleucine, molar ratio of L-Isoleucine to daptomycin is 1:1, and targeted pH of aqueous formulations according to the present disclosure before drying is from 4.5 to 7.0.

In one aspect, the daptomycin formulation before drying comprises 1% w/V or less of L-Isoleucine, molar ratio of L-Isoleucine to daptomycin is 1:1, and targeted pH of aqueous formulations according to the present disclosure before drying is from 4.5 to 7.0.

In one aspect, the daptomycin formulation before drying comprises 2.4% w/V or less of L-Valine targeted pH of aqueous formulations according to the present disclosure before drying is from 4.5 to 7.0.

In one aspect, the daptomycin formulation before drying comprises 2.4% w/V or less of L-Valine, molar ratio of L-Valine to daptomycin is 1:3, and targeted pH of aqueous formulations according to the present disclosure before drying is from 4.5 to 7.0.

In one aspect, the daptomycin formulation before drying comprises 2.4% w/V or less of L-Valine, molar ratio of L-Valine to daptomycin is 1:1, and targeted pH of aqueous formulations according to the present disclosure before drying is from 4.5 to 7.0.

In one aspect, the daptomycin formulation before drying comprises 1% w/V or less of L-Valine, molar ratio of L-Valine to daptomycin is 1:1, and targeted pH of aqueous formulations according to the present disclosure before drying is from 4.5 to 7.0.

In one aspect, targeted pH of aqueous formulations according to the present disclosure before drying is from 5.0 to 6.5.

In one aspect, the daptomycin formulation before drying comprises 2.4% w/V or less of at least one branched aliphatic amino acid and targeted pH of aqueous formulations according to the present disclosure before drying is from 5.0 to 6.5.

In one aspect, the daptomycin formulation before drying comprises 2.4% w/V or less of at least one branched aliphatic amino acid and targeted pH of aqueous formulations according to the present disclosure before drying is from 5.0 to 6.5 and where solid formulation of daptomycin has improved reconstitution time presented as for 60% to 96% reduced reconstitution time compared to the reconstitution time of Cubicin RLD.

In one aspect, the daptomycin formulation before drying comprises 2.4% w/V or less of at least one branched aliphatic amino acid and targeted pH of aqueous formulations according to the present disclosure before drying is from 5.0 to 6.5 and where solid formulation of daptomycin has improved reconstitution time presented as for 80% to 96% reduced reconstitution time compared to the reconstitution time of Cubicin RLD.

In one aspect, the daptomycin formulation before drying comprises 1% w/V or less of at least one branched aliphatic amino acid and targeted pH of aqueous formulations according to the present disclosure before drying is from 5.0 to 6.5.

In one aspect, the daptomycin formulation before drying comprises 2.4% w/V or less of L-Isoleucine and targeted pH of aqueous formulations according to the present disclosure before drying is from 5.0 to 6.5.

In one aspect, the daptomycin formulation before drying comprises 2.4% w/V or less of L-Isoleucine, molar ratio of L-Isoleucine to daptomycin is 1:1, and targeted pH of aqueous formulations according to the present disclosure before drying is from 5.0 to 6.5.

In one aspect, the daptomycin formulation before drying comprises 1% w/V or less of L-Isoleucine, molar ratio of L-Isoleucine to daptomycin is 1:1, and targeted pH of aqueous formulations according to the present disclosure before drying is from 5.0 to 6.5.

In one aspect, the daptomycin formulation before drying comprises 2.4% w/V or less of L-Valine and targeted pH of aqueous formulations according to the present disclosure before drying is from 5.0 to 6.5.

In one aspect, the daptomycin formulation before drying comprises 2.4% w/V or less of L-Valine, molar ratio of L-Valine to daptomycin is 1:1, and targeted pH of aqueous formulations according to the present disclosure before drying is from 5.0 to 6.5.

In one aspect, the daptomycin formulation before drying comprises 1% w/V or less of L-Valine, molar ratio of L-Valine to daptomycin is 1:1, and targeted pH of aqueous formulations according to the present disclosure before drying is from 5.0 to 6.5.

In one aspect, targeted pH of aqueous formulations according to the present disclosure before drying is from 5.0 to 6.5 and the improved reconstitution time of solid daptomycin formulation is 150 or less seconds.

In one aspect, the daptomycin formulation before drying comprises 2.5% w/V or less of the excipient for reducing reconstitution time, targeted pH of aqueous formulations according to the present disclosure before drying is from 5.0 to 6.5 and the improved reconstitution time of solid daptomycin formulation is 150 or less seconds.

In one aspect, the daptomycin formulation before drying comprises 1% w/V or less of the excipient for reducing reconstitution time, targeted pH of aqueous formulations according to the present disclosure before drying is from 5.0 to 6.5 and the improved reconstitution time of solid daptomycin formulation is 150 or less seconds.

In one aspect, the daptomycin formulation before drying comprises 1% w/V or less of the excipient for reducing reconstitution time, targeted pH of aqueous formulations according to the present disclosure before drying is from 5.0 to 6.5 and the improved reconstitution time of solid daptomycin formulation is 120 or less seconds.

In one aspect, the daptomycin formulation before drying comprises 1% w/V or less of L-Ile, targeted pH of aqueous formulations according to the present disclosure before drying is from 5.0 to 6.5 and the improved reconstitution time of solid daptomycin formulation is 90 or less seconds.

In one aspect, targeted pH of aqueous formulations according to the present disclosure before drying is from 5.0 to 6.4.

In one aspect, the daptomycin formulation before drying comprises 2.4% w/V or less of at least one branched aliphatic amino acid and targeted pH of aqueous formulations according to the present disclosure before drying is from 5.0 to 6.4.

In one aspect, the daptomycin formulation before drying comprises 2.4% w/V or less of at least one branched aliphatic amino acid and targeted pH of aqueous formulations according to the present disclosure before drying is from 5.0 to 6.4 and where solid formulation of daptomycin has improved reconstitution time presented as for 60% to 96% reduced reconstitution time compared to the reconstitution time of Cubicin RLD.

In one aspect, the daptomycin formulation before drying comprises 2.4% w/V or less of at least one branched aliphatic amino acid and targeted pH of aqueous formulations according to the present disclosure before drying is from 5.0 to 6.4 and where solid formulation of daptomycin has improved reconstitution time presented as for 80% to 96% reduced reconstitution time compared to the reconstitution time of Cubicin RLD.

In one aspect, the daptomycin formulation before drying comprises 1% w/V or less of at least one branched aliphatic amino acid and targeted pH of aqueous formulations according to the present disclosure before drying is from 5.0 to 6.4.

In one aspect, targeted pH of aqueous formulations according to the present disclosure before drying is from 5.0 to 6.2.

In one aspect, the daptomycin formulation before drying comprises 2.4% w/V or less of at least one branched aliphatic amino acid and targeted pH of aqueous formulations according to the present disclosure before drying is from 5.0 to 6.2.

In one aspect, the daptomycin formulation before drying comprises 2.4% w/V or less of at least one branched aliphatic amino acid and targeted pH of aqueous formulations according to the present disclosure before drying is from 5.0 to 6.2 and where solid formulation of daptomycin has improved reconstitution time presented as for 80% to 96% reduced reconstitution time compared to the reconstitution time of Cubicin RLD.

In one aspect, the daptomycin formulation before drying comprises 2.4% w/V or less of L-Isoleucine and targeted pH of aqueous formulations according to the present disclosure before drying is from 5.0 to 6.2.

In one aspect, the daptomycin formulation before drying comprises 2.4% w/V or less of L-Isoleucine, molar ratio of L-Isoleucine to daptomycin is 1:1, and targeted pH of aqueous formulations according to the present disclosure before drying is from 5.0 to 6.2.

In one aspect, the daptomycin formulation before drying comprises 1% w/V or less of L-Isoleucine, molar ratio of L-Isoleucine to daptomycin is 1:1, and targeted pH of aqueous formulations according to the present disclosure before drying is from 5.0 to 6.2.

In one aspect, the daptomycin formulation before drying comprises 1% w/V or less of L-Valine and targeted pH of aqueous formulations according to the present disclosure before drying is from 5.0 to 6.2.

In one aspect, the daptomycin formulation before drying comprises 1% w/V or less of L-Valine, molar ratio of L-Valine to daptomycin is 1:1, and targeted pH of aqueous formulations according to the present disclosure before drying is from 5.0 to 6.2.

In one aspect, targeted pH of aqueous formulations according to the present disclosure before drying is from 5.0 to 6.2 and the improved reconstitution time of solid daptomycin formulation is 150 or less seconds.

In one aspect, targeted pH of aqueous formulations according to the present disclosure before drying is from 5.4 to 6.2 and the improved reconstitution time of solid daptomycin formulation is 120 or less seconds.

In one aspect, the daptomycin formulation before drying comprises 2.4% w/V or less of at least one branched aliphatic amino acid, targeted pH of aqueous formulations according to the present disclosure before drying is from 5.0 to 6.2 and the improved reconstitution time of solid daptomycin formulation is 150 or less seconds.

In one aspect, the daptomycin formulation before drying comprises 2.4% w/V or less of at least one branched aliphatic amino acid, targeted pH of aqueous formulations according to the present disclosure before drying is from 5.4 to 6.2 and the improved reconstitution time of solid daptomycin formulation is 120 or less seconds.

In one aspect, the daptomycin formulation before drying comprises 1% w/V or less of at least one branched aliphatic amino acid, targeted pH of aqueous formulations according to the present disclosure before drying is from 5.0 to 6.2 and the improved reconstitution time of solid daptomycin formulation is 150 or less seconds.

In one aspect, the daptomycin formulation before drying comprises 1% w/V or less of at least one branched aliphatic amino acid, targeted pH of aqueous formulations according to the present disclosure before drying is from 5.4 to 6.2 and the improved reconstitution time of solid daptomycin formulation is 120 or less seconds.

In one aspect, the daptomycin formulation before drying comprises 1% w/V or less of at least one branched aliphatic amino acid, targeted pH of aqueous formulations according to the present disclosure before drying is from 5.0 to 6.2 and the improved reconstitution time of solid daptomycin formulation is 90 or less seconds.

In one aspect, the daptomycin formulation before drying comprises 1% w/V or less of L-Isoleucine, targeted pH of aqueous formulations according to the present disclosure before drying is from 5.0 to 6.2 and the improved reconstitution time of solid daptomycin formulation is 120 or less seconds.

In one aspect, the daptomycin formulation before drying comprises 1% w/V or less of L-Isoleucine, molar ratio of L-Isoleucine to daptomycin is 1:1, targeted pH of aqueous formulations according to the present disclosure before drying is from 5.0 to 6.2 and the improved reconstitution time of solid daptomycin formulation is 120 or less seconds.

In one aspect of the present disclosure, targeted pH of formulations according to the present disclosure before drying is from 5.0 to 7.0.

In one aspect of the present disclosure, targeted pH of formulations according to the present disclosure before drying is from 5.0 to 6.7.

In one aspect, the daptomycin formulation before drying comprises 2.4% w/V or less of at least one branched aliphatic amino acid and targeted pH of aqueous formulations according to the present disclosure before drying is from 5.0 to 7.0.

In one aspect, the daptomycin formulation before drying comprises 2.4% w/V or less of at least one branched aliphatic amino acid and targeted pH of aqueous formulations according to the present disclosure before drying is from 5.0 to 7.0 and where solid formulation of daptomycin has improved reconstitution time presented as for 60% to 96% reduced reconstitution time compared to the reconstitution time of Cubicin RLD.

In one aspect, the daptomycin formulation before drying comprises 2.4% w/V or less of at least one branched aliphatic amino acid and targeted pH of aqueous formulations according to the present disclosure before drying is from 5.0 to 7.0 and where solid formulation of daptomycin has improved reconstitution time presented as for 80% to 96% reduced reconstitution time compared to the reconstitution time of Cubicin RLD.

In one aspect, the daptomycin formulation before drying comprises 1% w/V or less of at least one branched aliphatic amino acid and targeted pH of aqueous formulations according to the present disclosure before drying is from 5.0 to 7.0.

In one aspect, the daptomycin formulation before drying comprises 2.4% w/V or less of L-Isoleucine and targeted pH of aqueous formulations according to the present disclosure before drying is from 5.0 to 7.0.

In one aspect, the daptomycin formulation before drying comprises 2.4% w/V or less of L-Isoleucine, molar ratio of L-Isoleucine to daptomycin is 1:1, and targeted pH of aqueous formulations according to the present disclosure before drying is from 5.0 to 7.0.

In one aspect, the daptomycin formulation before drying comprises 1% w/V or less of L-Isoleucine, molar ratio of L-Isoleucine to daptomycin is 1:1, and targeted pH of aqueous formulations according to the present disclosure before drying is from 5.0 to 7.

In one aspect, the daptomycin formulation before drying comprises 2.4% w/V or less of L-Valine and targeted pH of aqueous formulations according to the present disclosure before drying is from 5.0 to 7.0.

In one aspect, the daptomycin formulation before drying comprises 2.4% w/V or less of L-Valine, molar ratio of L-Valine to daptomycin is 1:1, and targeted pH of aqueous formulations according to the present disclosure before drying is from 5.0 to 7.0.

In one aspect, the daptomycin formulation before drying comprises 1% w/V or less of L-Valine, molar ratio of L-Valine to daptomycin is 1:1, and targeted pH of aqueous formulations according to the present disclosure before drying is from 5.0 to 7.0.

In one aspect, targeted pH of aqueous formulations according to the present disclosure before drying is from 5.0 to 7.0 and the improved reconstitution time of solid daptomycin formulation is 150 or less seconds.

In one aspect, the daptomycin formulation before drying comprises 2.5% w/V or less of the excipient for reducing reconstitution time, targeted pH of aqueous formulations according to the present disclosure before drying is from 5.0 to 7.0 and the improved reconstitution time of solid daptomycin formulation is 150 or less seconds.

In one aspect, the daptomycin formulation before drying comprises 1% w/V or less of the excipient for reducing reconstitution time, targeted pH of aqueous formulations according to the present disclosure before drying is from 5.0 to 7.0 and the improved reconstitution time of solid daptomycin formulation is 150 or less seconds.

In one aspect, the daptomycin formulation before drying comprises 1% w/V or less of the excipient for reducing reconstitution time, targeted pH of aqueous formulations according to the present disclosure before drying is from 5.0 to 7.0 and the improved reconstitution time of solid daptomycin formulation is 120 or less seconds.

In one aspect of the present disclosure, targeted pH of formulations according to the present disclosure before drying is from 6 to 7.

In one aspect of the present disclosure, targeted pH of formulations according to the present disclosure before drying is from 5.8 to 6.5.

In one aspect of the present disclosure, targeted pH of formulations according to the present disclosure before drying is from 5.8 to 6.4.

In one aspect, the daptomycin formulation before drying comprises 2.4% w/V or less of at least one branched aliphatic amino acid and targeted pH of aqueous formulations according to the present disclosure before drying is from 5.8 to 6.5.

In one aspect, the daptomycin formulation before drying comprises 2.4% w/V or less of at least one branched aliphatic amino acid and targeted pH of aqueous formulations according to the present disclosure before drying is from 5.8 to 6.5 and where solid formulation of daptomycin has improved reconstitution time presented as for 60% to 96% reduced reconstitution time compared to the reconstitution time of Cubicin RLD.

In one aspect, the daptomycin formulation before drying comprises 2.4% w/V or less of at least one branched aliphatic amino acid and targeted pH of aqueous formulations according to the present disclosure before drying is from 5.8 to 6.5 and where solid formulation of daptomycin has improved reconstitution time presented as for 80% to 96% reduced reconstitution time compared to the reconstitution time of Cubicin RLD.

In one aspect, the daptomycin formulation before drying comprises 1% w/V or less of at least one branched aliphatic amino acid and targeted pH of aqueous formulations according to the present disclosure before drying is from 5.8 to 6.5.

In one aspect, the daptomycin formulation before drying comprises 2.4% w/V or less of L-Isoleucine and targeted pH of aqueous formulations according to the present disclosure before drying is from 5.8 to 6.5.

In one aspect, the daptomycin formulation before drying comprises 2.4% w/V or less of L-Isoleucine, molar ratio of L-Isoleucine to daptomycin is 1:1, and targeted pH of aqueous formulations according to the present disclosure before drying is from 5.8 to 6.5.

In one aspect, the daptomycin formulation before drying comprises 1% w/V or less of L-Isoleucine, molar ratio of L-Isoleucine to daptomycin is 1:1, and targeted pH of aqueous formulations according to the present disclosure before drying is from 5.8 to 6.5.

In one aspect, the daptomycin formulation before drying comprises 2.4% w/V or less of L-Valine and targeted pH of aqueous formulations according to the present disclosure before drying is from 5.8 to 6.5.

In one aspect, the daptomycin formulation before drying comprises 2.4% w/V or less of L-Valine, molar ratio of L-Valine to daptomycin is 1:1, and targeted pH of aqueous formulations according to the present disclosure before drying is from 5.8 to 6.5.

In one aspect, the daptomycin formulation before drying comprises 1% w/V or less of L-Valine, molar ratio of L-Valine to daptomycin is 1:1, and targeted pH of aqueous formulations according to the present disclosure before drying is from 5.8 to 6.5.

In one aspect, targeted pH of aqueous formulations according to the present disclosure before drying is from 5.8 to 6.5 and the improved reconstitution time of solid daptomycin formulation is 150 or less seconds.

In one aspect, the daptomycin formulation before drying comprises 2.5% w/V or less of the excipient for reducing reconstitution time, targeted pH of aqueous formulations according to the present disclosure before drying is from 5.8 to 6.5 and the improved reconstitution time of solid daptomycin formulation is 150 or less seconds.

In one aspect, the daptomycin formulation before drying comprises 1% w/V or less of the excipient for reducing reconstitution time, targeted pH of aqueous formulations according to the present disclosure before drying is from 5.8 to 6.5 and the improved reconstitution time of solid daptomycin formulation is 150 or less seconds.

In one aspect, the daptomycin formulation before drying comprises 1% w/V or less of the excipient for reducing reconstitution time, targeted pH of aqueous formulations according to the present disclosure before drying is from 5.8 to 6.5 and the improved reconstitution time of solid daptomycin formulation is 120 or less seconds.

In one aspect, the daptomycin formulation before drying comprises 1% w/V or less of L-Ile, targeted pH of aqueous formulations according to the present disclosure before drying is from 5.8 to 6.5 and the improved reconstitution time of solid daptomycin formulation is 90 or less seconds.

All of the numbers used herein are modified by the term "about." This means that each number includes minor variations as defined ±10% of the numerical.

As used herein, the term "targeted pH" is defined as ±0.1 of the numerical value or range in question.

"pH" is the conventional measurement unit of hydrogen ion activity in a solution at room temperature, unless another temperature is specified.

In one aspect, targeted pH of formulations according to the present disclosure before drying is from 6.0 to 6.5.

In one aspect, targeted pH of formulations according to the present disclosure before drying is 4.5, 4.6, 4.7, 4.8, 4.9, 5.0, 5.1, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0. In one aspect, targeted pH of formulations according to the present disclosure before drying is 6.2.

As used herein, "aqueous composition" or "aqueous solutions" means any solution in which water is the main solvent (equal or above 50% V/V). Aqueous solutions include, but are not limited to solutions comprising 50%, 60%, 70%, 80%, 85%, 90%, 95%, 98% or 99% V/V water. Aqueous solutions can comprise a pharmaceutically acceptable organic solvent like ethanol, glycerol, propylene glycol, polyethylene glycols (PEG 200. PEG 300. PEG 400. 20 PEG 600. PEG 4000 etc.). Aqueous solutions can comprise 50% V/V or less of a pharmaceutically acceptable organic solvent.

It is known that the dry Daptomycin product on the market (i.e. Cubist RLD) is stable at refrigerated conditions of 2-8 degrees Celsius. In one aspect of the disclosure, solid daptomycin formulations comprising branched aliphatic amino acids as excipients for reducing reconstitution time may have comparable stability on refrigerated conditions as the dry Daptomycin product on the market (i.e. Cubist RLD). In one aspect, solid daptomycin formulations comprising branched aliphatic amino acids as excipients for reducing reconstitution time may have comparable stability at refrigerated conditions as the same daptomycin formulation but not having any excipients for reducing reconstitution time.

In case of storing daptomycin formulations of the present disclosure at temperatures higher than 2-8 degrees Celsius, there may be a need for adding of an "excipient for stabilization". The expression "excipient for stabilization" as used herein is to be understood to mean an excipient which may provide a stable daptomycin formulation on the temperature conditions which are higher than refrigerated temperature conditions.

In one aspect, the formulation may further include at least one excipient for stabilization.

In one aspect, the formulation may further include at least one excipient for stabilization of a solid formulation at room temperature conditions.

In one aspect, excipients for stabilization can be selected from sugars, sugar alcohols, amino sugars, organic solvents, divalent cations or cyclodextrins, or their pharmaceutically acceptable salts or derivatives thereof.

In one aspect, the formulation of the present disclosure comprises excipients for stabilization selected from non-reducing sugars such as sucrose, trehalose, maltose.

In one aspect, the formulation of the present disclosure may include divalent cations, such as sodium, calcium, magnesium or potassium. In one aspect of the present disclosure, the formulation of the present disclosure may include calcium which can be selected from calcium chloride ($CaCl_2$)), calcium chloride dihydrate, calcium chloride hexahydrate, calcium citrate, Ca-α-D-heptagluconate or calcium acetate.

In one aspect of the present disclosure, the source of calcium is comprised in molar ratio to daptomycin from 0.5:1 to 3:1, such as 0.5:1, 1:1, 2:1 or 3:1.

In one aspect, solid daptomycin formulation of the present disclosure may include at least one excipient for stabilization selected from amino acids, excluding branched aliphatic amino acids. In one aspect, solid daptomycin formulation of the present disclosure at least one excipient for stabilization may include Alanine, Arginine, Asparagine, Histidine, Glycine, Lysine, Ornithine, Phenylalanine, Proline, Threonine, Tryptophan, Tyrosine or its pharmaceutically acceptable salts or derivatives thereof.

In one aspect, solid daptomycin formulation of the present disclosure may include at least one excipient for stabilization selected from Arginine or Histidine.

In one aspect, formulation comprises at least Arginine, its pharmaceutically acceptable salt or derivative thereof. In one aspect, formulation further comprise Histidine, its pharmaceutically acceptable salt or derivative thereof. In one aspect, formulation further comprises Histidine hydrochloride.

In one aspect, daptomycin formulation further includes Arginine and Histidine, their pharmaceutically acceptable salts, or derivatives thereof.

In one aspect, at least one excipient for stabilization is comprised in molar ratio to daptomycin from 1:1 to 5:1. In one aspect, at least one excipient for stabilization is comprised in molar ratio to daptomycin of 1:1, 2:1, 3:1, 4:1, 5:1.

In one aspect, at least one excipient for stabilization is comprised in molar ratio to daptomycin from 3:1 to 5:1.

In one aspect, daptomycin formulation further includes Arginine and Histidine, their pharmaceutically acceptable salts or derivatives thereof, wherein molar ratio of daptomycin to the excipients Dapt:Arg:His is from 1:1:1 to 1:5:5.

In one aspect, solid formulation of daptomycin comprises comprising excipient for improving reconstitution time selected from L-Isoleucine, L-Valine or L-Leucine and at least one excipient for stabilization selected from Arginine and Histidine, their pharmaceutically acceptable salts or derivatives thereof.

In one aspect, solid formulation of daptomycin comprises excipient for improving reconstitution time selected from Isoleucine and at least one excipient for stabilization selected from Arginine and Histidine, their pharmaceutically acceptable salts, or derivatives thereof.

In one aspect, solid formulation of daptomycin comprises excipient for improving reconstitution time selected from Leucine and at least one excipient for stabilization selected from Arginine and Histidine, their pharmaceutically acceptable salts or derivatives thereof.

In one aspect, solid formulation of daptomycin comprises excipient for improving reconstitution time selected from Isoleucine and two excipients for stabilization and where first excipient for stabilization is Arginine and a second excipient for stabilization is Histidine or its pharmaceutically acceptable salts or derivatives thereof.

In one aspect, solid formulation of daptomycin comprises excipient for improving reconstitution time selected from Isoleucine and excipient for stabilization selected from Arginine and Histidine, wherein molar ratio of daptomycin to the excipients Dapt:Ile:Arg:His is from 1:0.5:1:1 to 1:3:5:5.

In one aspect, solid formulation of daptomycin comprises excipient for improving reconstitution time selected from Isoleucine and excipient for stabilization selected from Arginine and Histidine, wherein molar ratio of daptomycin to the excipients Dapt:Ile:Arg:His is 1:1:5:3.

In one aspect, solid formulation of daptomycin comprises excipient for improving reconstitution time selected from Valine and excipients for stabilization selected from Arginine and Histidine, wherein molar ratio of daptomycin to the excipients Dapt:Val:Arg:His is from 1:1:1:1 to 1:3:5:5.

In one aspect, solid formulation of daptomycin comprises excipient for improving reconstitution time selected from Valine and excipients for stabilization selected from Arginine and Histidine, wherein molar ratio of daptomycin to the excipients Dapt:Val:Arg:His is 1:1:5:3.

In one aspect, solid formulation of daptomycin comprises excipient for improving reconstitution time selected from Valine and excipients for stabilization selected from Arginine and Histidine, wherein molar ratio of daptomycin to the excipients Dapt:Val:Arg:His is 1:3:5:3.

In one aspect, solid formulation of daptomycin comprises excipient for improving reconstitution time selected from Isoleucine and excipients for stabilization selected from Arginine and Histidine, wherein molar ratio of daptomycin to the excipients Dapt:Ile:Arg:His is 1:1:4:3.

In one aspect, solid formulation of daptomycin comprises excipient for improving reconstitution time selected from Isoleucine and excipients for stabilization selected from Arginine and Histidine, wherein molar ratio of daptomycin to said excipients Dapt:Ile:Arg:His is 1:3:4:3.

In one aspect, solid formulation of daptomycin having improved reconstitution time comprises excipient for reduction reconstitution time selected from L-Isoleucine, L-Valine or L-Leucine and excipients for stabilization and where improved reconstitution time is presented as a reduction of reconstitution time of 25% or more compared to reconstitution time of the same solid daptomycin formulation comprising excipients for stabilization as disclosed herein but not comprising excipients for improved reconstitution time selected from L-Isoleucine, L-Valine or L-Leucine.

In one aspect, solid formulation of daptomycin having improved reconstitution time comprises excipient for improving reconstitution time selected from L-Isoleucine and excipients for stabilization selected from Arginine and Histidine and where improved reconstitution time is presented as a reduction of reconstitution time of 50% or more compared to reconstitution time of the same solid daptomycin formulation comprising excipients for stabilization selected from Arginine and Histidine but not comprising excipients for improved reconstitution time selected from L-Isoleucine, L-Valine or L-Leucine.

In one aspect, solid formulation of daptomycin having improved reconstitution time comprises excipient for improving reconstitution time selected from L-Isoleucine and excipients for stabilization selected from Arginine and Histidine, wherein molar ratio of daptomycin to said excipients Dapt:Ile:Arg:His is from 1:0.5:1:1 to 1:3:5:5 and where improved reconstitution time is presented as a reduction of reconstitution time of 75% or more compared to reconstitution time of the same solid daptomycin formulation but not comprising L-Isoleucine.

In one aspect, solid formulation of daptomycin having improved reconstitution time comprises excipient for improving reconstitution time selected from L-Isoleucine and excipients for stabilization selected from Arginine and Histidine, wherein molar ratio of daptomycin to said excipients Dapt:Ile:Arg:His is 1:1:5:3 and where improved reconstitution time is presented as a reduction of reconstitution time of 75% or more compared to reconstitution time of the same solid daptomycin formulation comprising excipients for stabilization selected from Arginine and Histidine in molar ratio of daptomycin to said excipients Dapt:Arg:His is 1:5:3 but not comprising L-Isoleucine.

In one aspect, solid formulation of daptomycin having improved reconstitution time comprises excipient for improving reconstitution time selected from L-Isoleucine and excipients for stabilization selected from Arginine and Histidine, wherein molar ratio of daptomycin to said excipients Dapt:Ile:Arg:His is 1:1:5:3 and where improved reconstitution time is presented as a reduction of reconstitution time of 70% or more compared to reconstitution time of the solid daptomycin formulation consisting of excipients for stabilization selected from Arginine and Histidine in molar ratio of daptomycin to said excipients Dapt:Arg:His is 1:5:3.

In one aspect, solid formulation of 500 mg Daptomycin having improved reconstitution time comprises excipient for improving reconstitution time selected from L-Isoleucine and excipients for stabilization selected from Arginine and Histidine, wherein molar ratio of daptomycin to said excipients Dapt:Ile:Arg:His is 1:1:5:3 and where improved reconstitution time is presented as a reduction of reconstitution time of 70% or more compared to reconstitution time of the solid daptomycin formulation consisting of excipients for stabilization selected from Arginine and Histidine in molar ratio of daptomycin to said excipients Dapt:Arg:His is 1:5:3 and where reconstitution of both formulations was performed in 10 mL of Water for injection at controlled room temperature (i.e. 20-25 degrees Celsius).

In one aspect, solid formulation of daptomycin having improved reconstitution time comprises excipient for improving reconstitution time selected from L-Isoleucine and excipients for stabilization selected from Arginine and Histidine, wherein molar ratio of daptomycin to said excipients Dapt:Ile:Arg:His is 1:3:5:3 and where improved reconstitution time is presented as a reduction of reconstitution time of 75% or more compared to reconstitution time of the same solid daptomycin formulation comprising excipients for stabilization selected from Arginine and Histidine, wherein molar ratio of daptomycin to said excipients is Dapt:Arg:His 1:5:3 but not L-Isoleucine.

In one aspect, solid formulation of daptomycin having improved reconstitution time comprises excipient for improving reconstitution time selected from L-Isoleucine and excipients for stabilization selected from Arginine and Histidine, wherein molar ratio of daptomycin to said excipients is Dapt:Ile:Arg:His 1:3:5:3 and where improved reconstitution time is presented as a reduction of reconstitution time of 70% or more compared to reconstitution time of solid daptomycin formulation consisting of excipients for stabilization selected from Arginine and Histidine, wherein molar ratio of daptomycin to said excipients is Dapt:Arg:His 1:5:3.

In one aspect, solid formulation of daptomycin having improved reconstitution time comprises excipient for improving reconstitution time selected from L-Isoleucine and excipients for stabilization selected from Arginine and Histidine, wherein molar ratio of daptomycin to said excipients Dapt:Ile:Arg:His is 1:1:4:3 and where improved reconstitution time is presented as a reduction of reconstitution time of 80% or more compared to reconstitution time of the same solid daptomycin formulation comprising excipients for stabilization selected from Arginine and Histidine, wherein molar ratio of daptomycin to said excipients Dapt:Arg:His is 1:4:3 not comprising L-Isoleucine.

Unless otherwise stated, it should be noted that all results for comparisons of reconstitution time referred to herein are obtained using the same conditions, such as temperature conditions, reconstitution agents and volume of reconstitution agent.

In one aspect, solid formulation of daptomycin comprises Isoleucine, Arginine and Histidine, wherein molar ratio of daptomycin to said excipients Dapt:Ile:Arg:His is 1:1:5:3 and wherein reconstitution time for 500 mg of solid daptomycin formulation in 10 mL of Water for injection at controlled room temperature (i.e. 20-25 degrees Celsius) is 50 seconds or less.

In one aspect, solid formulation of daptomycin comprises Isoleucine, Arginine and Histidine, wherein molar ratio of daptomycin to said excipients Dapt:Ile:Arg:His is 1:1:5:3 and wherein reconstitution time for 500 mg of solid daptomycin formulation in 10 mL of Water for injection at controlled room temperature (i.e. 20-25 degrees Celsius) is 50 seconds or less.

In one aspect, solid formulation of daptomycin comprises Isoleucine, Arginine and Histidine, wherein molar ratio of daptomycin to said excipients Dapt:Ile:Arg:His is 1:1:5:3 and wherein reconstitution time for 500 mg of solid daptomycin formulation in 10 mL of Water for injection at controlled room temperature (i.e. 20-25 degrees Celsius) is 45 seconds or less.

In one aspect, solid formulation of daptomycin comprises Isoleucine, Arginine and Histidine, wherein molar ratio of daptomycin to said excipients Dapt:Ile:Arg:His is 1:1:5:3 and wherein reconstitution time for 500 mg of solid daptomycin formulation in 10 mL of 0.9% sodium chloride at controlled room temperature (i.e. 20-25 degrees Celsius) is 45 seconds or less.

In one aspect, solid formulation of daptomycin comprises Isoleucine, Arginine and Histidine, wherein molar ratio of daptomycin to said excipients Dapt:Ile:Arg:His is 1:1:5:3 and wherein reconstitution time for 350 mg of solid daptomycin formulation in 7 mL of Water for injection at controlled room temperature (i.e. 20-25 degrees Celsius) is 60 seconds or less.

In one aspect, solid formulation of daptomycin comprises Isoleucine, Arginine and Histidine, wherein molar ratio of daptomycin to said excipients Dapt:Ile:Arg:His is 1:1:5:3 and wherein reconstitution time for 3.5 g of solid daptomycin formulation in 70 mL of Water for injection at controlled room temperature (i.e. 20-25 degrees Celsius) is 90 seconds or less.

In one aspect, solid formulation of daptomycin comprises Isoleucine, Arginine and Histidine, wherein molar ratio of daptomycin to said excipients Dapt:Ile:Arg:His is 1:1:4:3 and wherein reconstitution time for 500 mg of solid daptomycin formulation in 10 mL of Water for injection at controlled room temperature (i.e. 20-25 degrees Celsius) is 40 seconds or less.

In one aspect, the daptomycin formulation before drying comprises 10% w/V of daptomycin, 0.8% w/V of L-Isoleucine, 2.9% Histidine and 5.4% Arginine and has reconstitution time after drying of 45 seconds or less.

In one aspect, solid formulations of daptomycin can be stored at refrigerated conditions such as 2-8° C.

In one aspect, solid formulations of daptomycin comprising excipients for stabilization may achieve excellent stability which is not affected by temperature and humidity, thus it may be stored for a long time, easily prepared for a formulation for injection, and it is not decomposed by the influence of temperature and humidity during the manufacturing process.

In one aspect, formulations provided herein can be stored at room temperature (25° C.), below room temperature, such as temperature of 20° C., 15° C., 10° C., and refrigerated conditions such as 2-8° C.

As used herein, "stable" is defined either as no more than 10% of increase of total impurities formation, determined by HPLC analysis, or as no more than 5% of increase of every individual impurity formation, determined by HPLC analysis, under typical storage conditions after a predetermined time period.

For example, a stable or stabilized formulation can be one which has not more than 1%, 2%, 3%, 4%, 5%, 6%, 7%, 8%, 9%, 10%, of increase of total impurities formation after a predetermined time.

In one aspect of the present disclosure, reconstituted formulation of daptomycin may be stable for at least 4 days 2-8 degrees centigrade. In one aspect of the present disclosure, a reconstituted formulation of daptomycin may be stable for at least 48 hours on room temperature conditions.

According to the present disclosure, disclosed solid formulations of daptomycin are stable over the course of typical storage conditions, including time periods of 7 days (1 week), 14 days (2 weeks), 30 days (1 month), 60 days (2 months), 150 days (5 months), 180 days (6 months), 12 months (1 year) and longer at refrigerated conditions, for example, 2-8° C.

According to the present disclosure, disclosed solid formulations of daptomycin comprising excipients for stabilization are stable over the course of typical storage conditions, including time periods of 7 days (1 week), 14 days (2 weeks), 30 days (1 month), 60 days (2 months), 150 days (5 months), 180 days (6 months), 12 months (1 year) and longer at temperatures of 25° C. (room temperature), below room temperatures.

In one aspect, solid formulations of the present disclosure may be stored at room temperature, e.g. 25° C. for a predetermined period of time.

In one aspect, suitable pH adjusters used prior to drying or during reconstitution are hydrochloric acid or sodium hydroxide.

Not being bound by the above stated, other pH adjusters known and commonly used by one of ordinary skill in the art to which this disclosure belongs are also included herein.

In one aspect, solid formulation of daptomycin can further include other excipients selected from antioxidants, surfactants, lipids, complexing agents, preservatives, bulking agents, buffers, diluents, vehicles, solubilizers and binders etc. In view of excipients, as used herein, "pharmaceutically acceptable" is meant that they are useful in preparing a pharmaceutical composition that is generally non-toxic and neither biologically nor otherwise undesirable, further that they do not cause unacceptable loss of pharmacological activity of the drug in question, and are acceptable for use in treatment of humans and/or animals.

The solid formulations of the present disclosure can be reconstituted by known solutions for reconstitution.

The "reconstitution solutions" of interest herein is one which is pharmaceutically acceptable; safe and non-toxic for administration to a human, and is compatible for the preparation of a diluted formulation.

The formulations described herein may be further diluted in order to achieve lower therapeutically effective concentrations and according to the disclosure.

Exemplary solutions applicable both for reconstitution and dilution include sterile water for injection, sterile saline solution and Lactated Ringer's Injection solution.

For example, in a typical preparation of diluted formulations, the appropriate volume of the reconstituted formulation needed for the required therapeutically effective dose can be aseptically withdrawn and transferred into an infusion bag of a suitable solution, such as 0.225%, 0.45% or 0.9% Sodium Chloride, or Sterile Water for Injection or Lactated Ringer's Injection and administrated to a patient via appropriate route of administration.

Reconstituted formulations of solid daptomycin comprise therapeutically effective amounts of daptomycin, wherein therapeutically effective amounts include concentrations ranging from 0.5 mg/mL to 500 mg/mL, from 20 mg/mL to 400 mg/mL, from 50 mg/mL to 300 mg/mL, such as concentration of 0.5 mg/mL, 1 mg/mL, 3 mg/mL, 5 mg/mL, 8 mg/mL, 10 mg/mL, 15 mg/mL, 20 mg/mL, 23 mg/mL, 25 mg/mL, 30 mg/mL, 33 mg/mL, 35 mg/mL, 40 mg/mL, 50 mg/mL, 60 mg/mL, 70 mg/mL, 80 mg/mL, 90 mg/mL, 100 mg/mL, 110 mg/mL, 120 mg/mL, 130 mg/mL, 140 mg/mL, 150 mg/mL, 160 mg/mL, 170 mg/mL, 180 mg/mL, 190 mg/mL, 200 mg/mL, 220 mg/mL, 240 mg/mL, 260 mg/mL, 280 mg/mL, 300 mg/mL, 350 mg/mL, 400 mg/mL, 450 mg/mL and 500 mg/mL.

The language "therapeutically effective amount" or "therapeutically effective concentrations" of the daptomycin compound, as used herein, refers to an amount of reconstituted daptomycin administered to a patient sufficient to produce a therapeutic response to one or more of the symptoms of the disease being treated.

The reconstituted solutions of the disclosure have a pH which may vary between 5.5 and 7.

Solid formulations of daptomycin described herein could be administered via injection, for example subcutaneously, intracutaneously, intravenously, intramuscularly, intraarticularly, intrasynovially, intrasternally, intrathecally, intralesionally, intracranially or via intravenous infusion.

In one aspect, compositions are prepared by a process of mixing a solution of daptomycin and at least one branched aliphatic amino acid, adjusting the pH of such solution to pH from 4 to 9 with a suitable pH adjusting agent and lyophilizing or spray drying or fluid bed drying such composition.

In one aspect, compositions are prepared by a process of mixing a solution of daptomycin and at least one branched aliphatic amino acid, adjusting the pH of such solution. In one aspect, pH is adjusted from 5 to 6.5 with a suitable pH adjusting agent and lyophilizing or spray drying or fluid bed drying such composition.

In one aspect, compositions are prepared by a process of mixing a solution of daptomycin and at least one branched aliphatic amino acid, adjusting the pH of such solution to pH from 4.5 to 7 with a suitable pH adjusting agent and lyophilizing or spray drying or fluid bed drying such composition.

In one aspect, a solid formulation of daptomycin is prepared by lyophilizing an aqueous daptomycin solution comprising at least one excipient selected from branched aliphatic amino acid and wherein the liquid daptomycin solution has a targeted pH of 5.8 to 6.5.

In one aspect, a solid formulation of daptomycin is prepared by lyophilizing an aqueous liquid daptomycin solution comprising at least one excipient selected from branched aliphatic amino acid and wherein the liquid daptomycin solution has a pH of 6.2.

Present disclosure furthermore provides a method of improving reconstitution time of a solid formulation of daptomycin, where method comprises steps of mixing a solution of daptomycin and at least one branched aliphatic amino acid and drying of such composition.

Present disclosure furthermore provides a method of improving reconstitution time of a solid formulation of daptomycin, where method comprises steps of mixing a solution of daptomycin and L-Isoleucine and drying of such composition.

In one aspect, the method for reducing reconstitution time of the solid formulation of daptomycin, where method comprises steps of mixing a solution of daptomycin and L-Isoleucine, where concentration of L-Isoleucine is 1% w/V or less and drying of such composition.

In one aspect, the method for reducing reconstitution time of the solid formulation of daptomycin, where method comprises steps of mixing a solution daptomycin and L-Isoleucine, where concentration of L-Isoleucine 0.8% w/V and drying of such composition.

Also within the scope of the disclosure are uses of pharmaceutical formulations of daptomycin, as disclosed herein, for treating diseases caused by Gram positive bacteria such as complicated skin and soft-tissue infections (cSSTI), *Staphylococcus aureus* bloodstream infections (bacteremia), including those with right-sided infective endocarditis (RIE).

These uses comprise administering to the patient a therapeutically effective amount of formulations according to this disclosure or administering to the patient a therapeutically effective amount of preparation prepared from a pharmaceutical formulation of the present disclosure. E.g. the disclosure includes administering a pharmaceutically effective amount of a reconstituted solution and optionally further diluted solution of the solid pharmaceutically acceptable formulation according to the present disclosure.

Unless otherwise defined, all technical and scientific terms used herein have the same meaning as commonly understood by one of ordinary skill in the art to which this disclosure belongs.

The following examples are provided by way of illustration only and should not be construed to limit the scope of the disclosure.

Methods

Compositions according to this disclosure were prepared by providing a liquid solution of daptomycin and at least one excipient for reducing reconstitution time, adjusting the pH of such solutions with a suitable pH adjusting agent to a desired pH, transferring such solutions to vials to achieve desired amount of daptomycin per vial and lyophilization.

After lyophilization, initial time point level of impurities was determined by HPLC and afterwards vials were loaded to stability chambers at different storage conditions, such as 60° C., 25° C./60% RH and 40° C./75% RH.

Reconstitution time was measured after lyophilization (initial), wherein vials were reconstituted with 10.0 mL of WFI.

In order to determine impurities formation level and stability of daptomycin in formulations according to the present disclosure, vials were taken from stability chambers at various time points such as 45 hours, 1 month, 2 months etc. and analyzed by HPLC.

Analysis of the formulations of the present disclosure can be performed using techniques known in the art such as HPLC technique, including HPLC such as disclosed in WO2011063419.

LIST OF ABBREVIATIONS USED

DAP—Daptomycin
RH—Relative humidity
WFI—Water for injection
D—Day(s)
M—Month(s)
W—Week(s)
Arg—Arginine
His—Histidine
Ile—Isoleucine
Leu—Leucine
Val—Valine
$TP_n$—Value of total impurities at time point different than initial, for example: 45 hrs, 1 month, 2 months etc. at different storage conditions such as 25° C./60% RH, 40° C./75% RH and 60° C., determined by HPLC
Δ—Calculated increase of total impurities: Δ Total impurities (%)=Total impurities value at $TP_n$(%)—Total impurities initial value (%)
Total impurities %—Calculated using Area percentage method:
A determination of the level of analyte, As, compared with the total area of all the sample-related peaks in the chromatogram, Σ(As)i $$\text{Area \% of } As=[As/\Sigma(As)i]\times 100$$

EXAMPLE 1

Daptomycin (10.423 g, given the assay on anhydrous basis of daptomycin of 97.7% and water content of 1.8%), was added in WFI solution comprising excipient for reconstitution. Molar ratio varied from molar ratio of daptomycin to the excipient for reconstitution of 1:0.5 to 1:3, such as 1:0.5, 1:1 and 1:3. In some of the formulations, excipients for stabilization were also added.

The contents were then stirred using a magnetic stirrer. pH was adjusted using 6M HCl and/or 1M NaOH solution to 6.2. The solution was then transferred to a volumetric flask and WFI was added to make up to volume of 100 mL.

The solution was mixed to ensure homogeneity, filtered through a 0.2 μm filter, transferred to vials and lyophilized.

Reconstitution time as presented in Table 1a refers to the time required for 500 mg of the lyophilized daptomycin to dissolve in 10 mL of 0.9% sodium chloride at controlled room temperature (20-25 degrees ° C.). Given is the comparative reconstitution time for RLD (Cubicin) vs Xellia in-house developed daptomycin generic product vs various formulations of the present disclosure. Xellia in-house developed daptomycin generic product does not comprise excipient for reduction of reconstitution according to the present disclosure and it is stored on refrigerated conditions. Reconstitution time as showed in Table 1a is a maximum reconstitution time measured at several samples of each formulation under the same conditions.

TABLE 1a

Reconstitution times of 500 mg of daptomycin formulations with 10 mL of 0.9% sodium chloride

| Formulation Molar ratio to excipient for reducing reconstitution time | Reconstitution time min:sec |
|---|---|
| DAP Cubicin RLD 1:0 | 15:34 |
| DAP Xellia 500 mg 1:0 | 13:38 |
| DAP:Ile = 1:0.5 | 1:21 |
| DAP:Ile = 1:1 | 2:00 |
| DAP:Ile = l:3 | 2:28 |
| DAP:Leu = 1:1.5 | 1:52 |
| DAP:Val = 1:3 | 1:02 |
| Dap:Val = 1:1 | 1:38 |
| DAP: L-His: L-Arg:Ile = 1:3:4:1 | 0:35 |
| DAP:L-His:L-Arg:Ile = 1:3:5:1 | 0:50 |

From the table 1a it is visible that solid formulation comprising branched aliphatic amino acids have reduced reconstitution time with respect to the compared reconstitution time of daptomycin formulations on the market. According to the table 1a, reconstitution time of the daptomycin formulations presented in the table is reduced from 82% to 96%.

Reconstitution time as presented in Table 1b refers to the time required for 500 mg of the lyophilized daptomycin to dissolve in 10 mL of Water for injection at controlled room temperature (20-25 degrees ° C.). Given is the comparative reconstitution time for daptomycin formulations having excipients for stability with or without excipients for reducing reconstitution time. Reconstitution time as showed in Table 1a is a maximum reconstitution measured at several samples for each of formulations under the same conditions.

TABLE 1b

Reconstitution times of 500 mg of daptomycin in 10 ml of WFI

| Formulation Molar ratio | Reconstitution time |
|---|---|
| DAP:L-His:L-Arg = 1:3:5 | 3:10 |
| DAP:L-His:L-Arg = 1:3:4 | 3:15 |
| DAP:L-His:L-Arg:Ile = 1:3:5:3 | 0:40 |
| DAP:L-His:L-Arg:Ile = 1:3:5:1 | 0:45 |
| DAP:L-His:L-Arg:Ile = 1:3:4:1 | 0:35 |

From the table 1b it is visible that solid formulation comprising Ile has reduced reconstitution time with respect to the same formulation not having Ile by 76% or even 82%.

EXAMPLE 2

Daptomycin (10.423 g, given the assay on anhydrous basis of daptomycin of 97.7% and water content of 1.8%), was added in WFI solution comprising excipient for reconstitution. Molar ratio varied from molar ratio of daptomycin to the excipient for reconstitution of 1:0.5 to 1:1.5, such as 1:0.5, 1:1 and 1:1.5.

The contents were then stirred using a magnetic stirrer. pH shown in tables was adjusted using 6M HCl solution. The solution was then transferred to a volumetric flask and WFI was added to make up to volume of 100 mL.

The solution was mixed to ensure homogeneity, filtered through a 0.2 μm filter, transferred to vials and lyophilized.

Reconstitution time as presented in Table 2a and 2b refers to the time required for 500 mg of the lyophilized daptomycin to dissolve in 10 mL of Water for injection (table 2a) and 0.9% NaCl (Table 2b) at controlled room temperature (20-25 degrees ° C.). Given is the comparative reconstitution time for pH range of 5.0 to 5.8 for various formulations of the present disclosure. Reconstitution time as showed in Tables 2a and 2b is a maximum reconstitution time measured at several samples of each formulation under the same conditions.

TABLE 2

Reconstitution times of 500 mg of daptomycin in 10 ml of WFI

| Formulation Molar ratio | pH of the composition prior to drying | Reconstitution time |
|---|---|---|
| DAP:L-Val = 1:1 | 5.8 | 1:43 |
| DAP:L-Val = 1:1 | 5.4 | 1:05 |
| DAP:L-Leu = 1:1.5 | 5.8 | 1:28 |
| DAP:L-Ile = 1:0.5 | 5.8 | 1:16 |
| DAP:L-Ile = 1:1 | 5.4 | 1:30 |
| DAP:L-Val = 1:1 | 5.0 | 2:10 |

TABLE 2b

Reconstitution times of 500 mg of daptomycin in 10 ml of 0.9% NaCl

| Formulation Molar ratio | pH of the composition prior to drying | Reconstitution time |
|---|---|---|
| DAP:L-Ile = 1:1 | 5.4 | 1:45 |
| DAP:L-Val = 1:1 | 5.0 | 1:50 |

EXAMPLE 3

Daptomycin (10.423 g, given the assay on anhydrous basis of daptomycin of 97.7% and water content of 1.8%), was added in WFI solution comprising excipient for reconstitution. Arginine and Histidine are added as excipients for stabilization of the formulation on room temperature conditions.

The contents were then stirred using a magnetic stirrer. pH was adjusted using 6M HCl and/or 1M NaOH solution. The solution was then transferred to a volumetric flask and WFI was added to make up to volume of 100 mL.

The solution was mixed to ensure homogeneity, filtered through a 0.2 μm filter, transferred to vials and lyophilized.

Reconstitution time as presented in Table 3a refers to the time required for lyophilized daptomycin of weight as specified in the Table 3a to dissolve at controlled room temperature (20-25 degrees ° C.). Reconstitution time as showed in Table 3a is a maximum reconstitution time measured at several samples of each formulation under the same conditions.

TABLE 3a

Reconstitution times of different quantity of daptomycin in WFI

| Formulation Molar ratio | pH of the composition prior to drying | Rec. agent volume | Daptomycin formulation quantity | Reconstitution time |
|---|---|---|---|---|
| DAP:L-His:L-Arg: Ile = 1:3:5:1 | 6.2 | 7 ml | 350 mg | 0:57 |
| DAP:L-His:L-Arg: Ile = 1:3:5:1 | 6.2 | 70 ml | 3.5 g | 1:30 |

TABLE 3b

Reconstitution time during storage

| Formulation Molar ratio | pH of the composition prior to drying | Time point of reconstitution | Reconstitution time |
|---|---|---|---|
| DAP:L-His:L-Arg:Ile = 1:3:5:1 | 6.3 | Start | 0:43 |
| | 6.3 | 1 month | 0:30 |
| | 6.4 | 2 months | 0:25 |

Reconstitution time as presented in Table 3b refers to the time required for 350 mg lyophilized daptomycin solution to dissolve in 7 mL of water for injection at controlled room temperature at start and after certain periods of storage on same temperature conditions. Reconstitution time as showed in Table 3b is a maximum reconstitution time measured at several samples of each formulation under the same conditions.

EXAMPLE 4—STABILITY OF SOLID FORMULATIONS OF DAPTOMYCIN IN REFRIGERATED CONDITIONS

Solid formulations of Daptomycin are prepared by adding Daptomycin into WFI solution comprising excipient for reconstitution. Molar ratio varied from molar ratio of daptomycin to the excipient for reconstitution of 1:0.5 to 1:3, such as 1:0.5, 1:1 and 1:3.

The contents are stirred using a magnetic stirrer. pH is adjusted using 6M HCl and/or 1M NaOH solution to various pH values from 5.0 to 6.5. The solution is transferred to a volumetric flask and WFI is added to make up to volume of 100 mL.

The solution is mixed to ensure homogeneity, filtered through a 0.2 μm filter, transferred to vials and lyophilized.

Lyophilized formulations are then stored on 2-8° C. and stability is determined on time points such as 1 month, 2 months, 3 months, 6 months, 12 months and further.

It is expected that the formulations are stable for 3 and 6 months at 2-8° C., and that this can be extrapolated to indicate that the formulations are stable or stabilized for up to about 24 months.

EXAMPLE 5

The following numbered items represent embodiments of liquid pharmaceutical formulations comprising active component.

Item 1. A solid pharmaceutical formulation of daptomycin comprising at least one branched aliphatic amino acid or their pharmaceutically acceptable salts or derivatives thereof.

Item 2. A solid pharmaceutical formulation of daptomycin according to item 1, wherein at least one branched aliphatic amino acid is an excipient for improving reconstitution time and where said branched aliphatic amino acid include Leucine, Isoleucine and Valine.

Item 3. A solid pharmaceutical formulation of daptomycin according to items 1 and 2, wherein the formulation has improved reconstitution time.

Item 4. A solid formulation of daptomycin according to item 2, wherein at least one branched aliphatic amino acid is selected from L-Leucine, L-Isoleucine and L-Valine.

Item 5. A solid formulation of daptomycin according to item 4, wherein at least one branched aliphatic amino acid is L-Isoleucine.

Item 6. A solid formulation of daptomycin according to item 4, wherein at least one branched aliphatic amino acid is L-Valine.

Item 7. A solid formulation of daptomycin according to item 4, wherein at least one branched aliphatic amino acid is L-Leucine.

Item 8. A solid formulation of daptomycin according to any of items 1 to 7, wherein the branched aliphatic amino acid is comprised in formulation prior to drying in an amount of 2.5% w/V or less.

Item 9. A solid formulation of daptomycin according to any of items 1 to 7, wherein branched aliphatic amino acid is comprised in formulation prior to drying in an amount of 1% w/V or less.

Item 10. A solid formulation of daptomycin according to item 5, wherein the formulation before drying comprises 10% w/V of daptomycin and 0.8% w/V of L-Isoleucine.

Item 11. A solid formulation of daptomycin according to any of items 1 to 10, wherein pH of the formulation prior to drying is from 4.5 to 9.

Item 12. A solid formulation of daptomycin according to any of items 1 to 10, wherein pH of the formulation prior to drying is from 4.5 to 7.0.

Item 13. A solid formulation of daptomycin according to any of items 1 to 10, wherein pH of the formulation prior to drying is from 5.0 to 6.2.

Item 14. A solid formulation of daptomycin according to any of items 1 to 10, wherein pH of the formulation prior to drying is 6.2.

Item 14. A solid formulation of daptomycin according to any of items 1 to 10, wherein pH of the formulation prior to drying is from 5.8 to 6.5.

Item 16. A solid formulation of daptomycin according to any of items 1 to 10, wherein pH of the formulation prior to drying is from 5.0 to 6.5.

Item 17. A solid formulation of daptomycin according to any of items 1 to 16, wherein at least one branched aliphatic amino acid is comprised in solid formulation of daptomycin in molar ratio to daptomycin from 0.5:1 to 5:1.

Item 18. A solid formulation of daptomycin according to any of items 1 to 16, wherein at least one branched aliphatic amino acid is comprised in solid formulation of daptomycin in molar ratio to daptomycin of from 1:1 to 3:1.

Item 19. A solid formulation of daptomycin according to any of items 1 to 16, wherein at least one branched aliphatic amino acid is comprised in solid formulation of daptomycin in molar ratio to daptomycin of 1:1.

Item 20. A solid formulation of daptomycin according to any one of items from 1 to 19, where reconstitution time of the formulation is less than 120 seconds.

Item 21. A solid formulation of daptomycin according to any one of items from 1 to 19, wherein pH of the formulation prior to drying is from 5.0 to 6.2, and where reconstitution time of the formulation is less than 120 seconds.

Item 22. A solid formulation of daptomycin according to any one of items from 1 to 19, where reconstitution time of 500 mg of the solid pharmaceutical daptomycin formulation in 10 mL of 0.9% sodium chloride at controlled room temperature is less than 120 seconds.

Item 23. A solid formulation of daptomycin according to any one of items from 1 to 19, wherein pH of the formulation prior to drying is from 4.5 to 7.0 and where reconstitution time of 500 mg of the solid pharmaceutical daptomycin formulation in 10 mL of Water for injection at controlled room temperature is less than 120 seconds.

Item 24. A solid formulation of daptomycin according to any one of items from 1 to 19, wherein pH of the formulation prior to drying is from 5.0 to 6.2 and where reconstitution time of 500 mg of the solid pharmaceutical daptomycin formulation in 10 mL of Water for injection at controlled room temperature is less than 120 seconds.

Item 25. A solid formulation of daptomycin according to any one of items 1 to 19, wherein improved reconstitution time is presented as from 60% to 96% reduced reconstitution time compared to the reconstitution time of Cubicin RLD.

Item 26. A solid formulation of daptomycin according to any one of items 1 to 19, wherein improved reconstitution time is presented as from 80% to 96% reduced reconstitution time compared to the reconstitution time of Cubicin RLD.

Item 27. A solid formulation of daptomycin according to any one of items from 1 to 26, where formulation is stable for a predetermined period of time on 2-8° C.

Item 28. A solid formulation of daptomycin according to any one of items from 1 to 19, comprising at least one excipient for stabilization.

Item 29. A solid formulation of daptomycin according to item 28, where formulation is stable for a predetermined period of time on room temperature conditions comprising at least one excipient for stabilization.

Item 30. A solid formulation of daptomycin according to items 27 or 29, where predetermined period of time include 7 days (1 week), 14 days (2 weeks), 30 days (1 month), 60 days (2 months), 150 days (5 months), 180 days (6 months), 12 months (1 year) and longer.

Item 31. A solid formulation of daptomycin according to item 30, where predetermined period of time is 6 months.

Item 32. A solid formulation of daptomycin according to item 29, where at least one excipient for stabilization include Alanine, Arginine, Asparagine, Histidine, Glycine, Lysine, Ornithine, Phenylalanine, Proline, Treonine, Tryptophan, Tyrosine or its pharmaceutically acceptable salts or derivatives thereof.

Item 33. A solid formulation of daptomycin according to item 32, where at least one amino acid is selected from Arginine and Histidine, its pharmaceutically acceptable salts or derivatives thereof.

Item 34. A solid formulation of daptomycin according to items 32 and 32, where formulation comprises two excipients for stabilization and where first excipient for stabilization is Arginine and a second excipient for stabilization is Histidine or its pharmaceutically acceptable salts or derivatives thereof.

Item 35. A solid formulation of daptomycin according to any one of items 28 to 34, where excipient for stabilization is comprised in molar ratio to daptomycin from 3:1 to 5:1.

Item 36. A solid formulation of daptomycin according to item 32 to 34, where solid formulation of daptomycin comprises branched aliphatic amino acid as an excipient for improving reconstitution time selected from Isoleucine and at least one excipient for stabilization selected from Arginine and Histidine, their pharmaceutically acceptable salts or derivatives thereof.

Item 37. A solid formulation of daptomycin according to item 32 to 34, where solid formulation of daptomycin comprises excipient for improving reconstitution time selected from Leucine and two excipients for stabilization and where first excipient for stabilization is Arginine and a second excipient for stabilization is Histidine or its pharmaceutically acceptable salts or derivatives thereof.

Item 38. A solid formulation of daptomycin according to item 32 to 34, where solid formulation of daptomycin comprises excipient for improving reconstitution time selected from Valine and two excipients for stabilization and where first excipient for stabilization is Arginine and a second excipient for stabilization is Histidine or its pharmaceutically acceptable salts or derivatives thereof.

Item 39. A solid formulation of daptomycin according to item 32 or 36, where solid formulation of daptomycin comprises excipient for improving reconstitution time selected from Isoleucine and two excipients for stabilization selected from Arginine and Histidine, wherein molar ratio of daptomycin to the excipients Dapt:Ile:Arg:His is from 1:0.5:1:1 to 1:3:5:5.

Item 40. A solid formulation of daptomycin according to item 32 or 36, where solid formulation of daptomycin comprises excipient for improving reconstitution time selected from Isoleucine and two excipients for stabilization selected from Arginine and Histidine, wherein molar ratio of daptomycin to the excipients Dapt:Ile:Arg:His is 1:1:5:3.

Item 41. A solid formulation of daptomycin according to item 32 or 36, where solid formulation of daptomycin comprises excipient for improving reconstitution time selected from Isoleucine and two excipients for stabilization selected from Arginine and Histidine, wherein molar ratio of daptomycin to the excipients Dapt:Ile:Arg:His is 1:1:4:3.

Item 42. A solid formulation of daptomycin according to any one of items 32 to 36, where solid formulation of daptomycin comprises excipient for improving reconstitution time selected from L-Isoleucine and excipients for stabilization selected from Arginine and Histidine, wherein molar ratio of daptomycin to said excipients Dapt:Ile:Arg:His is 1:1:5:3 and where reconstitution time of 500 mg of solid formulation of daptomycin in 10 mL of Water for injection at controlled room temperature is 50 seconds or less.

Item 43. A solid formulation of daptomycin according to any one of items 32 to 36, where solid formulation of daptomycin comprises excipient for improving reconstitution time selected from L-Isoleucine and excipients for stabilization selected from Arginine and Histidine, wherein molar ratio of daptomycin to said excipients Dapt:Ile:Arg:His is 1:1:5:3 and where reconstitution time of 350 mg of solid formulation of daptomycin in 7 mL of Water for injection at controlled room temperature is 60 seconds or less.

Item 44. A solid formulation of daptomycin according to any one of items 32 to 36, where solid formulation of daptomycin comprises excipient for improving reconstitution time selected from L-Isoleucine and excipients for stabilization selected from Arginine and Histidine, wherein molar ratio of daptomycin to said excipients Dapt:Ile:Arg:His is 1:1:5:3 and where reconstitution time of 3500 mg of solid formulation of daptomycin in 70 mL of Water for injection at controlled room temperature is 90 seconds or less.

Item 45. A solid formulation of daptomycin according to any one of items 32 to 36, where solid formulation of daptomycin comprises excipient for improving reconstitution time selected from L-Isoleucine and excipients for stabilization selected from Arginine and Histidine, wherein molar ratio of daptomycin to said excipients Dapt:Ile:Arg:His is 1:1:4:3 and where reconstitution time of 500 mg of solid formulation of daptomycin in 10 mL of Water for injection at controlled room temperature is 50 seconds or less.

Item 46. A solid formulation of daptomycin according to any one of items 18 to 23, where solid formulation of daptomycin comprises excipient for improving reconstitution time selected from L-Isoleucine and excipients for stabilization selected from Arginine and Histidine, wherein molar ratio of daptomycin to said excipients Dapt:Ile:Arg:His is 1:1:5:3 and having improved reconstitution time where improved reconstitution time is presented as a reducing reconstitution time of 75% or more compared to reconstitution time of the same solid daptomycin formulation comprising excipients for stabilization selected from Arginine and Histidine, wherein molar ratio of daptomycin to said excipients Dapt:Arg:His is 1:5:3 but without L-Isoleucine.

Item 47. A solid formulation of daptomycin according to any one of items 32 to 36, where solid formulation of daptomycin comprises excipient for improving reconstitution time selected from L-Isoleucine and excipients for stabilization selected from Arginine and Histidine, wherein molar ratio of daptomycin to said excipients Dapt:Ile:Arg:His is 1:1:5:3 and having improved reconstitution time where improved reconstitution time is presented as a reducing reconstitution time of 70% or more compared to reconstitution time of solid daptomycin formulation consisting of excipients for stabilization selected from Arginine and Histidine, wherein molar ratio of daptomycin to said excipients Dapt:Ile:Arg:His is 1:5:3.

Item 48. A solid formulation of daptomycin according to any one of items 1 to 4, where solid formulation of daptomycin having improved reconstitution time comprises excipient for reduction reconstitution time selected from L-Isoleucine, L-Valine or L-Leucine and excipients for stabilization and where improved reconstitution time is presented as a reduction of reconstitution time of 25% or more compared to reconstitution time of the same solid daptomycin formulation comprising excipients for stabilization as disclosed herein but not comprising excipients for improved reconstitution time selected from L-Isoleucine, L-Valine or L-Leucine.

Item 49. A solid formulation of daptomycin according to any one of items 1 to 4, where solid formulation of daptomycin comprises at least one branched aliphatic amino acid selected from L-Isoleucine, L-Valine or L-Leucine, where daptomycin formulation before drying comprises 2.5% w/V or less of the branched aliphatic amino acid and pH of the formulation prior to drying is from 4.5 to 7.0.

Item 50. A solid formulation of daptomycin according to any one of items 1 to 4, where solid formulation of daptomycin comprises at least one branched aliphatic amino acid selected from L-Isoleucine, L-Valine or L-Leucine, where daptomycin formulation before drying comprises 2.4% w/V or less of the branched aliphatic amino acid and pH of the formulation prior to drying is from 5.0 to 6.2.

Item 51. A solid formulation of daptomycin according to any one of items 1 to 4, where solid formulation of daptomycin comprises at least one branched aliphatic amino acid selected from L-Isoleucine, L-Valine or L-Leucine, where daptomycin formulation before drying comprises 2.4% w/V or less of the branched aliphatic amino acid and pH of the formulation prior to drying is from 4.5 to 7.0 and where solid formulation of daptomycin has a reconstitution time of 180 seconds or less.

Item 52. A solid formulation of daptomycin according to any one of items 1 to 4, where solid formulation of daptomycin comprises at least one branched aliphatic amino acid selected from L-Isoleucine, L-Valine or L-Leucine, where daptomycin formulation before drying comprises 2.4% w/V or less of the branched aliphatic amino acid and pH of the formulation prior to drying is from 5.0 to 6.2 and where solid formulation of daptomycin has a reconstitution time of 150 seconds or less.

Item 53. A solid formulation of daptomycin according to any one of items 1 to 4, where solid formulation of daptomycin comprises at least one branched aliphatic amino acid selected from L-Isoleucine, L-Valine or L-Leucine, where daptomycin formulation before drying comprises 2.4% w/V or less of the branched aliphatic amino acid and pH of the formulation prior to drying is from 5.4 to 6.2 and where solid formulation of daptomycin has a reconstitution time of 120 seconds or less.

Item 54. A solid formulation of daptomycin according to any one of items 1 to 4, where solid formulation of daptomycin comprises L-Isoleucine, where L-Isoleucine is comprised in amount of 2.4% w/V or less prior to drying and pH of the formulation prior to drying is from 5.4 to 6.2 and where solid formulation of daptomycin has a reconstitution time of 120 seconds or less.

Item 55. A solid formulation of daptomycin according to any one of items 1 to 4, where solid formulation of daptomycin comprises L-Valine, where L-Valine is comprised in amount of 2.4% w/V or less prior to drying and pH of the formulation prior to drying is from 5.4 to 6.2 and where solid formulation of daptomycin has a reconstitution time of 120 seconds or less.

Item 56. A solid formulation of daptomycin according to any one of items 1 to 4, where solid formulation of daptomycin comprises at least one branched aliphatic amino acid selected from L-Isoleucine, L-Valine or L-Leucine, where daptomycin formulation before drying comprises 1% w/V or less of branched aliphatic amino.

Item 57. A solid formulation of daptomycin according to any one of items 1 to 4, where solid formulation of daptomycin comprises at least one branched aliphatic amino acid selected from L-Isoleucine, L-Valine or L-Leucine, where daptomycin formulation before drying comprises 2.4% w/V or less of branched aliphatic amino.

Item 58. A solid formulation of daptomycin according to any one of items 1 to 4, where solid formulation of daptomycin comprises at least one branched aliphatic amino acid selected from L-Isoleucine, L-Valine or L-Leucine, where daptomycin formulation before drying comprises 1% w/V or less of branched aliphatic amino and pH of the formulation prior to drying is from 4.5 to 7.0.

Item 59. A solid formulation of daptomycin, where solid formulation of daptomycin comprises at least one branched aliphatic amino acid selected from L-Isoleucine, L-Valine or L-Leucine, where daptomycin formulation before drying comprises 1% w/V or less of the branched aliphatic amino acid and pH of the formulation prior to drying is from 4.5 to 7.0 and where solid formulation of daptomycin has a reconstitution time of 180 seconds or less.

Item 60. A solid formulation of daptomycin, where solid formulation of daptomycin comprises at least one branched aliphatic amino acid selected from L-Isoleucine, L-Valine or L-Leucine, where daptomycin formulation before drying comprises 1% w/V or less of the branched aliphatic amino acid and pH of the formulation prior to drying is from 5.0 to 6.2.

Item 61. A solid formulation of daptomycin, where solid formulation of daptomycin comprises at least one branched aliphatic amino acid selected from L-Isoleucine, L-Valine or L-Leucine, where daptomycin formulation before drying comprises 1% w/V or less of the branched aliphatic amino acid and pH of the formulation prior to drying is from 5.0 to 6.2 and where solid formulation of daptomycin has a reconstitution time od 150 seconds or less.

Item 62. A solid formulation of daptomycin, where solid formulation of daptomycin comprises at least one branched aliphatic amino acid selected from L-Isoleucine, L-Valine or L-Leucine, where daptomycin formulation before drying comprises 1% w/V or less of the branched aliphatic amino acid and pH of the formulation prior to drying is from 5.4 to 6.2 and where solid formulation of daptomycin has a reconstitution time of 120 seconds or less.

Item 63. A solid formulation of daptomycin, where solid formulation of daptomycin comprises L-Isoleucine, where daptomycin formulation before drying comprises 1% w/V or less of L-Isoleucine and pH of the formulation prior to drying is from 5.4 to 6.2 and where solid formulation of daptomycin has a reconstitution time of 120 seconds or less.

Item 64. A solid formulation of daptomycin, where solid formulation of daptomycin comprises L-Valine, daptomycin formulation before drying comprises 1% w/V or less of L-Valine and pH of the formulation prior to drying is from 5.4 to 6.2 and where solid formulation of daptomycin has a reconstitution time of 120 seconds or less.

Item 65. A solid formulation of daptomycin, where formulation comprises before drying 2.4% w/V or less of L-Valine and where solid formulation of daptomycin has improved reconstitution time presented as 60% to 96% reduced reconstitution time compared to the reconstitution time of Cubicin RLD.

Item 66. A solid formulation of daptomycin, where formulation comprises before drying 2.4% w/V or less of L-Valine and pH of the formulation prior to drying is from 4.5 to 7.0 and where solid formulation of daptomycin has improved reconstitution time presented as 60% to 96% reduced reconstitution time compared to the reconstitution time of Cubicin RLD.

Item 67. A solid formulation of daptomycin, where formulation comprises before drying 2.4% w/V or less of L-Valine and pH of the formulation prior to drying is from 5.0. to 6.2 and where solid formulation of daptomycin has improved reconstitution time presented as 82% to 96% reduced reconstitution time compared to the reconstitution time of Cubicin RLD.

Item 68. A solid formulation of daptomycin, where formulation comprises before drying 2.4% w/V or less of L-Isoleucine and where solid formulation of daptomycin has improved reconstitution time presented as 60% to 96% reduced reconstitution time compared to the reconstitution time of Cubicin RLD.

Item 69. A solid formulation of daptomycin, where formulation comprises before drying 2.4% w/V or less of L-Isoleucine and pH of the formulation prior to drying is from 5.0. to 7.0 and where solid formulation of daptomycin has improved reconstitution time presented as 60% to 96% reduced reconstitution time compared to the reconstitution time of Cubicin RLD.

Item 70. A solid formulation of daptomycin, where formulation comprises before drying 2.4% w/V or less of L-Isoleucine and pH of the formulation prior to drying is from 5.0. to 6.2 and where solid formulation of daptomycin has improved reconstitution time presented as for 82% or more reduced reconstitution time compared to the reconstitution time of Cubicin RLD.

Item 71. A solid formulation of daptomycin where solid formulation of daptomycin comprises Isoleucine, Arginine, Histidine, where formulation comprises before drying 2.4% w/V or less of Isoleucine and wherein molar ratio of daptomycin to the excipients Dapt:Ile:Arg:His is from 1:0.5:1:1 to 1:3:5:5.

Item 71. A solid formulation of daptomycin where solid formulation of daptomycin comprises Isoleucine, Arginine, Histidine, where formulation comprises before drying 2.4% w/V or less of Isoleucine and pH of the formulation prior to drying is from 4.5 to 7.0 and wherein molar ratio of daptomycin to the excipients Dapt:Ile:Arg:His is from 1:0.5:1:1 to 1:3:5:5.

Item 72. A solid formulation of daptomycin according to any one of items from 1 to 19, wherein pH of the formulation prior to drying is from 5.0 to 6.5, and where reconstitution time of the formulation is less than 120 seconds.

Item 73. A solid formulation of daptomycin according to any one of items 1 to 4, where solid formulation of daptomycin comprises at least one branched aliphatic amino acid selected from L-Isoleucine, L-Valine or L-Leucine, where daptomycin formulation before drying comprises 2.4% w/V or less of the branched aliphatic amino acid and pH of the formulation prior to drying is from 5.0 to 6.5.

Item 74. A solid formulation of daptomycin according to any one of items 1 to 4, where solid formulation of daptomycin comprises at least one branched aliphatic amino acid selected from L-Isoleucine, L-Valine or L-Leucine, where daptomycin formulation before drying comprises 2.4% w/V or less of the branched aliphatic amino acid and pH of the formulation prior to drying is from 5.0 to 6.5 and where solid formulation of daptomycin has a reconstitution time of 150 seconds or less.

Item 75. A solid formulation of daptomycin, where solid formulation of daptomycin comprises at least one branched aliphatic amino acid selected from L-Isoleucine, L-Valine or L-Leucine, where daptomycin formulation before drying comprises 1% w/V or less of the branched aliphatic amino acid and pH of the formulation prior to drying is from 5.0 to 6.5.

Item 76. A solid formulation of daptomycin, where solid formulation of daptomycin comprises at least one branched aliphatic amino acid selected from L-Isoleucine, L-Valine or L-Leucine, where daptomycin formulation before drying comprises 1% w/V or less of the branched aliphatic amino acid and pH of the formulation prior to drying is from 5.0 to 6.5 and where solid formulation of daptomycin has a reconstitution time of 150 seconds or less.

Item 77. A solid formulation of daptomycin, where formulation comprises before drying 2.4% w/V or less of L-Valine and pH of the formulation prior to drying is from 5.0. to 6.5 and where solid formulation of daptomycin has improved reconstitution time presented as 82% to 96% reduced reconstitution time compared to the reconstitution time of Cubicin RLD.

Item 78. A solid formulation of daptomycin, where formulation comprises before drying 2.4% w/V or less of L-Isoleucine and pH of the formulation prior to drying is from 5.0. to 6.5 and where solid formulation of daptomycin has improved reconstitution time presented as for 82% or more reduced reconstitution time compared to the reconstitution time of Cubicin RLD.

Item 79. A solid formulation of daptomycin where solid formulation of daptomycin comprises Isoleucine, Arginine, Histidine, where formulation comprises before drying 2.4% w/V or less of Isoleucine and pH of the formulation prior to drying is from 5.0 to 6.5 and wherein molar ratio of daptomycin to the excipients Dapt:Ile:Arg:His is from 1:0.5:1:1 to 1:3:5:5.

Item 80. A solid formulation of daptomycin according to any one of items from 1 to 19, wherein pH of the formulation prior to drying is from 5.8 to 6.5, and where reconstitution time of the formulation is less than 120 seconds.

Item 81. A solid formulation of daptomycin according to any one of items 1 to 4, where solid formulation of daptomycin comprises at least one branched aliphatic amino acid selected from L-Isoleucine, L-Valine or L-Leucine, where daptomycin formulation before drying comprises 2.4% w/V or less of the branched aliphatic amino acid and pH of the formulation prior to drying is from 5.8 to 6.5.

Item 82. A solid formulation of daptomycin according to any one of items 1 to 4, where solid formulation of daptomycin comprises at least one branched aliphatic amino acid selected from L-Isoleucine, L-Valine or L-Leucine, where daptomycin formulation before drying comprises 2.4% w/V or less of the branched aliphatic amino acid and pH of the formulation prior to drying is from 5.8 to 6.5 and where solid formulation of daptomycin has a reconstitution time of 150 seconds or less.

Item 83. A solid formulation of daptomycin, where solid formulation of daptomycin comprises at least one branched aliphatic amino acid selected from L-Isoleucine, L-Valine or L-Leucine, where daptomycin formulation before drying comprises 1% w/V or less of the branched aliphatic amino acid and pH of the formulation prior to drying is from 5.8 to 6.5.

Item 84. A solid formulation of daptomycin, where solid formulation of daptomycin comprises at least one branched aliphatic amino acid selected from L-Isoleucine, L-Valine or L-Leucine, where daptomycin formulation before drying comprises 1% w/V or less of the branched aliphatic amino acid and pH of the formulation prior to drying is from 5.8 to 6.5 and where solid formulation of daptomycin has a reconstitution time of 150 seconds or less.

Item 85. A solid formulation of daptomycin, where formulation comprises before drying 2.4% w/V or less of L-Valine and pH of the formulation prior to drying is from 5.8 to 6.5 and where solid formulation of daptomycin has improved reconstitution time presented as 82% to 96% reduced reconstitution time compared to the reconstitution time of Cubicin RLD.

Item 86. A solid formulation of daptomycin, where formulation comprises before drying 2.4% w/V or less of L-Isoleucine and pH of the formulation prior to drying is from 5.8 to 6.5 and where solid formulation of daptomycin has improved reconstitution time presented as for 82% or more reduced reconstitution time compared to the reconstitution time of Cubicin RLD.

Item 87. A solid formulation of daptomycin where solid formulation of daptomycin comprises Isoleucine, Arginine, Histidine, where formulation comprises before drying 2.4% w/V or less of Isoleucine and pH of the formulation prior to drying is from 5.8 to 6.5 and wherein molar ratio of daptomycin to the excipients Dapt:Ile:Arg:His is from 1:0.5:1:1 to 1:3:5:5.

Item 89. A method of producing a solid formulation of daptomycin according to any of above items, wherein the method comprises providing a solution of daptomycin and at least one branched aliphatic amino acid, adjusting the pH of such solution to pH from 4 to 9 with a suitable pH adjusting agent and lyophilizing or spray drying or fluid bed drying such composition.

Item 90. A method of improving reconstitution time of the solid formulation of daptomycin by using at least one branched aliphatic amino acid in preparing solid formulation of daptomycin.

The invention claimed is:

1. A solid pharmaceutically acceptable formulation of daptomycin, wherein said formulation is prepared by lyophilizing an aqueous daptomycin solution comprising daptomycin and at least one branched chain aliphatic amino acid or a pharmaceutically acceptable salt thereof, wherein the aliphatic side chain of the at least one branched chain aliphatic amino acid comprises a branch, and wherein a reconstitution time of 500 mg of the solid pharmaceutical daptomycin formulation in 10 mL of 0.9% sodium chloride at controlled room temperature is less than 120 seconds, wherein the solid formulation does not include an amino sugar.

2. The solid formulation of daptomycin according to claim 1, wherein the at least one branched chain aliphatic amino acid comprises Leucine, Isoleucine, or Valine.

3. The solid formulation of daptomycin according to claim 2, wherein the at least one branched chain aliphatic amino acid is selected from L-Leucine, L-Isoleucine, and L-Valine.

4. The solid formulation of daptomycin according to claim 3, wherein the at least one branched chain aliphatic amino acid is L-Isoleucine.

5. The solid formulation of daptomycin according to claim 3, wherein the at least one branched chain aliphatic amino acid is L-Valine.

6. The solid formulation of daptomycin according to claim 1, wherein the branched chain aliphatic amino acid, prior to lyophilizing, is present in an amount of 2.5% w/V or less.

7. The solid formulation of daptomycin according to claim 1, wherein the branched chain aliphatic amino acid, prior to lyophilizing, is present in an amount of 1% w/V or less.

8. The solid formulation of daptomycin according to claim 4, wherein the formulation prior to lyophilizing comprises 10% w/V of daptomycin and 0.8% w/V of L-Isoleucine.

9. The solid formulation of daptomycin according to claim 1, wherein a pH of the formulation prior to lyophilizing is from 4.5 to 9.

10. The solid formulation of daptomycin according claim 1, wherein a pH of the formulation prior to lyophilizing is from 6 to 6.5.

11. The solid formulation of daptomycin according to claim 1, wherein the at least one branched chain aliphatic amino acid is present in a molar ratio to daptomycin from 0.5:1 to 5:1.

12. The solid formulation of daptomycin according to claim 1, wherein the at least one branched chain aliphatic amino acid is present in a molar ratio to daptomycin from 1:1 to 3:1.

13. The solid formulation of daptomycin according to claim 4, having an improved reconstitution time from 60% to 96% compared to the reconstitution time of a solid daptomycin formulation which does not contain at least one branched chain aliphatic amino acid.

14. The solid formulation of daptomycin according to claim 4, having an improved reconstitution time from 80% to 96% compared to the reconstitution time of a solid daptomycin formulation which is stored in refrigerated conditions and has as an inactive ingredient only sodium hydroxide for pH adjustment.

15. The solid formulation of daptomycin according to claim 1, comprising at least one excipient for stabilization.

16. The solid formulation of daptomycin according to claim 15, wherein the at least one excipient for stabilization comprises Alanine, Arginine, Asparagine, Histidine, Glycine, Lysine, Ornithine, Phenylalanine, Proline, Threonine, Tryptophan, Tyrosine, or a pharmaceutically acceptable salt thereof.

17. The solid formulation of daptomycin according to claim 16, wherein the at least one excipient for stabilization is selected from Arginine, Histidine, or a pharmaceutically acceptable salt thereof.

18. The solid formulation of daptomycin according to claim 16, wherein the formulation comprises two excipients for stabilization, wherein a first excipient for stabilization is Arginine, or a pharmaceutically acceptable salt thereof, and a second excipient for stabilization is Histidine, or a pharmaceutically acceptable salt thereof.

19. The solid formulation of daptomycin according to claim 16, wherein the excipient for stabilization is present in a molar ratio to daptomycin from 3:1 to 5:1.

20. The solid formulation of daptomycin according to claim 16, wherein the solid formulation of daptomycin comprises Isoleucine, or a pharmaceutically acceptable salt thereof as the branched chain aliphatic amino acid, and at least one excipient for stabilization selected from Arginine, Histidine, or a pharmaceutically acceptable salt thereof.

21. The solid formulation of daptomycin according to claim 19, wherein the solid formulation of daptomycin comprises Isoleucine, or a pharmaceutically acceptable salt thereof as the branched chain aliphatic amino acid, and two excipients for stabilization that are Arginine, Histidine, or a pharmaceutically acceptable salt thereof, wherein a molar ratio of daptomycin to the excipients Dapt:Ile:Arg:His is from 1:0.5:1:1 to 1:3:5:5.

22. The solid formulation of daptomycin according to claim 19, wherein the solid formulation of daptomycin comprises Isoleucine, or a pharmaceutically acceptable salt thereof as the branched chain aliphatic amino acid, and two excipients for stabilization that are Arginine, Histidine, a pharmaceutically acceptable salt thereof, wherein a molar ratio of daptomycin to the excipients Dapt:Ile:Arg:His is 1:1:5:3.

23. The solid formulation of daptomycin according to claim 16, wherein the solid formulation of daptomycin comprises L-Isoleucine as the branched chain aliphatic amino acid, and an excipient for stabilization selected from Arginine and Histidine, wherein a molar ratio of daptomycin to said excipients Dapt:Ile:Arg:His is 1:1:5:3, and wherein a reconstitution time of 500 mg of solid formulation of daptomycin in 10 mL of water for injection at controlled room temperature is 50 seconds or less.

24. The solid formulation of daptomycin according to claim 16, wherein the solid formulation of daptomycin comprises L-Isoleucine as the branched chain aliphatic amino acid and an excipient for stabilization selected from Arginine and Histidine, wherein a molar ratio of daptomycin to said excipients Dapt:Ile:Arg:His is 1:1:5:3, wherein the formulation has an improved reconstitution time, wherein improved reconstitution time is a reduction of reconstitution time of 75% or more compared to a reconstitution time of a solid daptomycin formulation comprising excipients for stabilization selected from Arginine and Histidine, wherein a molar ratio of daptomycin to said excipients Dapt:Arg:His is 1:5:3.

25. A method of producing a solid formulation of daptomycin according to claim 1, wherein the method comprises providing a solution of the daptomycin and the at least one branched chain aliphatic amino acid, adjusting the pH of the solution to pH from 4 to 9 with a pH adjusting agent, and lyophilizing the solution.

26. A method of improving a reconstitution time of a solid formulation of daptomycin comprising providing at least one branched chain aliphatic amino acid in preparing the solid formulation of daptomycin.

27. The solid formulation of daptomycin according to claim 1, wherein the solid formulation does not include a surfactant, a sugar alcohol, an organic solvent, a divalent cation, a cyclodextrin, or a combination thereof.

* * * * *